United States Patent
Kojima

(10) Patent No.: US 7,476,761 B2
(45) Date of Patent: Jan. 13, 2009

(54) PROCESS FOR PRODUCING ACETIC ACID

(75) Inventor: Hidetaka Kojima, Himeji (JP)

(73) Assignee: Daicel Chemical Industries, Ltd., Sakai-Shi, Osaka (JP)

( * ) Notice: Subject to any disclaimer, the term of this patent is extended or adjusted under 35 U.S.C. 154(b) by 0 days.

(21) Appl. No.: 11/793,398

(22) PCT Filed: Dec. 14, 2005

(86) PCT No.: PCT/JP2005/023420

§ 371 (c)(1),
(2), (4) Date: Jun. 19, 2007

(87) PCT Pub. No.: WO2006/068157

PCT Pub. Date: Jun. 29, 2006

(65) Prior Publication Data

US 2008/0097124 A1     Apr. 24, 2008

(30) Foreign Application Priority Data

Dec. 20, 2004    (JP) .............................. 2004-368249

(51) Int. Cl.
*C07C 51/12*    (2006.01)
*C07C 53/08*    (2006.01)
(52) U.S. Cl. ...................................... 562/519; 562/607
(58) Field of Classification Search ........................ None
See application file for complete search history.

(56) References Cited

U.S. PATENT DOCUMENTS 5,663,430 A * 9/1997 Morris et al. ............... 562/608
5,939,585 A * 8/1999 Ditzel et al. ................ 562/519

FOREIGN PATENT DOCUMENTS

| EP | 0 728 727 A1 | 8/1996 |
| EP | 0 728 729 A1 | 8/1996 |
| JP | 60-054334 A | 3/1985 |
| JP | 60-155147 A | 8/1985 |
| JP | 60-239434 A | 11/1985 |
| JP | 8-5839 B2 | 1/1996 |

* cited by examiner

*Primary Examiner*—Karl J Puttlitz
(74) *Attorney, Agent, or Firm*—Birch, Stewart, Kolasch & Birch, LLP

(57) ABSTRACT

A process for producing a carboxylic acid comprises allowing an alcohol having a carbon number of "n" to continuously react with carbon monoxide in the presence of a carbonylation catalyst system, and a limited amount of water, continuously withdrawing the reaction mixture from the reaction system 1, introducing the withdrawn reaction mixture into a distillation step (distillation columns 3a and 3b), and separating a higher-boiling component and a lower-boiling component containing a carboxylic acid having a carbon number of "n+1", respectively. In the process, the amount of carbon monoxide and/or hydrogen contained in a liquid phase of the reaction system is adjusted to at least one of the following conditions (i) and (ii): (i) the amount of carbon monoxide relative to 1 kilogram of the liquid phase by weight is at least 2 mmol per 1 MPa of carbon monoxide partial pressure of the reaction system, and (ii) the amount of hydrogen relative to 1 kilogram of the liquid phase by weight is at least 50 mmol per 1 MPa of hydrogen partial pressure of the reaction system. Such a process inhibits deactivation of a metal catalyst and deterioration in a reaction rate, and decreases formation of by-products in producing a carboxylic acid under a low water content.

9 Claims, 4 Drawing Sheets

PROCESS FOR PRODUCING ACETIC ACID

TECHNICAL FIELD

The present invention relates to a process for producing a carboxylic acid (e.g., acetic acid) from an alcohol (e.g., methanol) and carbon monoxide. In particular, the present invention relates to a process for producing an industrially useful carboxylic acid, which can inhibit generation of a by-product and improves in a reaction rate even in the presence of water at a low content (e.g., not higher than 10% by weight, and particularly not higher than 5% by weight), and a method for improving a formation rate of a carboxylic acid.

BACKGROUND ART

Acetic acid is one of basic chemicals, and is important in the petrochemical industry, the industry of polymer chemistry, the organic chemical industry, and the pharmaceutical and agricultural manufacturing industry.

Acetic acid is produced by a variety of processes, and among others, a process for producing acetic acid from methanol and carbon monoxide is industrially superior to other processes.

In recent years, as an improved process for producing acetic acid from methanol and carbon monoxide, it has been proposed to improve productivity of acetic acid and reduce generation of by-products by reducing a water content in a reaction fluid. However, in the case where the water content in the reaction fluid is reduced, a rhodium catalyst is easy to precipitate, and it is unfavorable in catalyst activity or catalyst stability, and in addition, the reaction rate is easy to decrease. Therefore, it has been investigated to add an iodide salt such as lithium iodide to a reaction system, or to prevent the undesirable effects of lowering of a water content in a reaction fluid by using a specific catalyst system. For example, Japanese Patent Application Laid-Open No. 54334/1985 (JP-60-54334A) (Patent Document 1) discloses a process which comprises allowing an alcohol or a derivative thereof to react with carbon monoxide in the presence of water and a catalyst system containing a rhodium component and an alkyl halide component to produce a carboxylic acid, wherein, in the liquid-phase carbonylation reaction, an iodide is added to the catalyst system in order to maintain an iodine ion concentration of not less than 0.3 mol/l in the carbonylation reaction fluid. Japanese Patent Application Laid-Open No. 239434/1985 (JP-60-239434A) (Patent Document 2) discloses a process for producing a lower carboxylic acid which comprises allowing a lower alcohol to react with carbon monoxide in a reaction medium containing a rhodium catalyst, wherein the obtained lower carboxylic acid has one more carbon atom than the lower alcohol has. The process maintains at least a limited amount of water, and (a) an effective amount of a catalyst stabilizer (an iodide such as lithium iodide), (b) that of an iodide derivative of a lower hydrocarbon, and (c) that of an ester of the alcohol with the carboxylic acid, in the reaction medium. Japanese Patent Application Laid-Open No. 155147/1985 (JP-60-155147A) (Patent Document 3) discloses a process for producing an organic carboxylic acid which comprises allowing an alcohol to catalytically react with carbon monoxide in the presence of a homogeneous catalyst system composed of (a) an organic ester and (b) a rhodium metal atom and a mixture of lithium iodide and methyl iodide.

Moreover, Japanese Patent Publication No. 5839/1996 (JP-8-5839B) (Patent Document 4) discloses a process for producing a lower carboxylic acid which comprises allowing a feed composed of an alcohol essentially having one less carbon atom than the carboxylic acid has to react with carbon monoxide in a carbonylation reactor holding a liquid reaction medium containing a rhodium catalyst, wherein (a) an effective amount of a catalyst stabilizer (an iodide), (b) that of an iodide derivative of a lower hydrocarbon corresponding to the alcohol, (c) that of an ester of the carboxylic acid and the alcohol, and (d) at least 4 psi of hydrogen partial pressure in the reaction condition, as well as at least a limited amount of water are maintained in the reaction medium during the reaction. The patent document 4 mentions that increase in the hydrogen partial pressure enlarges the ratio Rh(I)/Rh(III) in the carbonylation reactor by a water-gas shift reaction, resulting in increase of a formation rate of acetic acid. Further, in the patent document 4, since the reaction rate significantly decreases at a water content of not more than 10% by weight in the reaction fluid, the reaction rate is increased by adding 5 to 30% by weight of lithium iodide. In such a process, however, since the proportion of Rh(I) relative to Rh(III) increases by keeping the hydrogen partial pressure of the reaction system not less than a certain pressure, the catalyst activity can be maintained to some extent. However, the hydrogen partial pressure is enhanced by supplying hydrogen to the reactor, and therefore generation of by-products (e.g., propionic acid, formic acid, and a hydrocarbon) increases even when the water content in reaction fluid is reduced. Further, in order to improve the space time yield, it is necessary to enhance the reaction pressure in the reactor or resupply carbon monoxide to a bottom solution of the reactor.

Patent Document 1: JP-60-54334A (claim 1)
Patent Document 2: JP-60-239434A (claim 1)
Patent Document 3: JP-60-155147A (claim 1)
Patent Document 4: JP-8-5839B (claim 1, FIGS. 3 and 4)

DISCLOSURE OF THE INVENTION

Problems to be Solved by the Invention

It is therefore an object of the present invention to provide a process for producing a carboxylic acid, which can reduce generation of a by-product without deterioration of a reaction rate even when a water content of a reaction system is low, and a method for improving a formation rate of a carboxylic acid.

Another object of the present invention is to provide a process for producing a carboxylic acid, which ensures to inhibit deactivation of a metal catalyst and deterioration in a reaction rate without enhancing a hydrogen partial pressure in a reactor needlessly, and a method for improving a formation rate of a carboxylic acid.

Means to Solve the Problems

The inventor of the present invention made various studies about production of acarboxylic acid from an alcohol or a derivative thereof and carbon monoxide, and revealed that, when a water content of a reaction system is low in a production process of a carboxylic acid, (1) a shift reaction between carbon monoxide and water is reduced and generation of hydrogen is remarkably decreased in quantity, and therefore, a low active Rh(III) catalyst is not smoothly converted to an active Rh(I) catalyst and the catalyst activity is deteriorated, and in addition, the catalyst component easily precipitates, and the reaction rate gradually decreases; and (2) such deterioration of the catalyst activity and reaction rate, and precipitation of the catalyst are particularly notable in a continuous reaction, and it is difficult to utilize such a process industrially. Therefore, the inventor of the present invention made intensive studies to achieve such problems (the above objects) and finally found that, in a process of producing a carboxylic acid by allowing an alcohol to continuously react with carbon monoxide under a low water content (e.g., not more than 10% by weight, in particular not more than 5% by weight), when a proportion of carbon monoxide contained in a liquid phase of the reaction system (an amount relative to 1 kilogram of the liquid phase by weight per 1 MPa of carbon monoxide partial pressure) and/or a proportion of hydrogen (an amount relative to 1 kilogram of the liquid phase by weight per 1 MPa of hydrogen partial pressure) is maintained within a specific range, the process ensures to inhibit deactivation of a catalyst, maintain the reaction rate, and prevent by-products from generating without enhancing a hydrogen partial pressure in a reactor needlessly. The present invention was accomplished based on the above findings.

That is, in the process for producing a carboxylic acid having a carbon number of "n+1" (e.g., acetic acid) according to the present invention, the process comprises allowing an alcohol having a carbon number of "n" or a derivative thereof to continuously react with carbon monoxide in the presence of a catalyst system comprising a metal catalyst component, and an alkyl halide and/or hydrogen halide, and a limited amount of water, continuously withdrawing the reaction mixture from the reaction system, introducing the withdrawn reaction mixture into a distillation step, and separating a higher-boiling component at least containing the metal catalyst component and a lower-boiling component containing a carboxylic acid having a carbon number of "n+1", respectively, wherein the amount of carbon monoxide and/or hydrogen contained in a liquid phase of the reaction system fulfills at least one of the following conditions (i) and (ii):

(i) the amount of carbon monoxide relative to 1 kilogram of the liquid phase by weight is at least 2 mmol per 1 MPa of carbon monoxide partial pressure of the reaction system, and (ii) the amount of hydrogen relative to 1 kilogram of the liquid phase by weight is at least 50 mmol per 1 MPa of hydrogen partial pressure of the reaction system.

In the production process, the reaction of the alcohol or the derivative thereof with carbon monoxide may be carried out in the presence of water of 0.1 to 10% by weight relative to the whole liquid phase of the reaction system. In the reaction system, a carbon monoxide partial pressure may be 0.9 to 3 MPa (e.g., 0.9 to 2 MPa), and a hydrogen partial pressure may be 0.01 to 0.1 MPa. In the production process, the reaction may be carried out in the presence of the catalyst system comprising a catalyst composed of a metal of the group 8 of the Periodic Table of Elements, an alkali metal iodide, and an alkyl iodide to produce acetic acid at a formation rate of at least 10 mol/L/h (mol/(L·h)) as a space time yield, and a liquid reaction mixture (or a reaction fluid) may be continuously withdrawn, and introduced into the distillation step having a pressure lower than the pressure of the reaction system. In the case where the carboxylic acid having a carbon number of "n+1" is acetic acid, the formation rate of acetaldehyde as a by-product may be one-1500th or less (e.g., one-2100th or less) as high as that of acetic acid.

The production process may comprise allowing methanol to continuously react with carbon monoxide in the presence of the catalyst system comprising a catalyst composed of a metal of the group 8 of the Periodic Table of Elements, lithium iodide and methyl iodide, and 0.1 to 5% by weight of water relative to the whole liquid phase in the reaction system to produce acetic acid, and in the process the amount of carbon monoxide contained in the liquid phase of the reaction system relative to 1 kilogram of the liquid phase by weight may be 2 to 50 mmol per 1 MPa of carbon monoxide partial pressure of the reaction system, the amount of hydrogen contained in the liquid phase of the reaction system relative to 1 kilogram of the liquid phase by weight may be 50 to 400 mmol per 1 MPa of hydrogen partial pressure of the reaction system, the formation rate of acetic acid may be at least 18 mol/L/h (mol/(L·h)) as a space time yield, and the formation rate of acetaldehyde as a by-product may be one-2300th or less as high as that of acetic acid.

In the production process, the distillation step may comprise a catalyst-separation step, and a carboxylic acid-purification step; the reaction mixture withdrawn from the reaction system may be introduced into the catalyst-separation step to separate the higher-boiling component containing the metal catalyst component and the lower-boiling component containing a carboxylic acid having a carbon number of "n+1", respectively; and the lower-boiling component may be introduced into the carboxylic acid-purification step to separate a higher-boiling impurity, a lower-boiling component containing a carboxylic acid having a carbon number of "n+1", and a waste gas component at least containing carbon monoxide and hydrogen, respectively.

The present invention also includes a method for inhibiting precipitation of a metal catalyst and generation of a by-product with improving a formation rate of a carboxylic acid in the above-mentioned process for producing the carboxylic acid, wherein the method comprises adjusting an amount of carbon monoxide and/or hydrogen contained in the liquid phase of the reaction system to at least one of the above-mentioned conditions (i) and (ii).

EFFECTS OF THE INVENTION

According to the present invention, since the proportion of carbon monoxide (the amount relative to 1 kilogram of the liquid phase by weight per 1 MPa of carbon monoxide partial pressure) and/or the proportion of hydrogen (the amount relative to 1 kilogram of the liquid phase by weight per 1 MPa of hydrogen partial pressure) contained in the liquid phase of the reaction system is maintained within a specific range, deterioration of the reaction rate can be inhibited and generation of the by-products can be effectively reduced even when the water content in the reaction system is low. Moreover, since deterioration of the catalyst activity can be inhibited without enhancing the hydrogen partial pressure in the reaction system needlessly, decrease in the reaction rate can be inhibited. Further, since it is unnecessary to enhance the hydrogen partial pressure in the reaction system more than requires, generation of by-products due to the rise of the hydrogen partial pressure can be also inhibited.

DETAILED DESCRIPTION OF THE INVENTION

Figure 1:
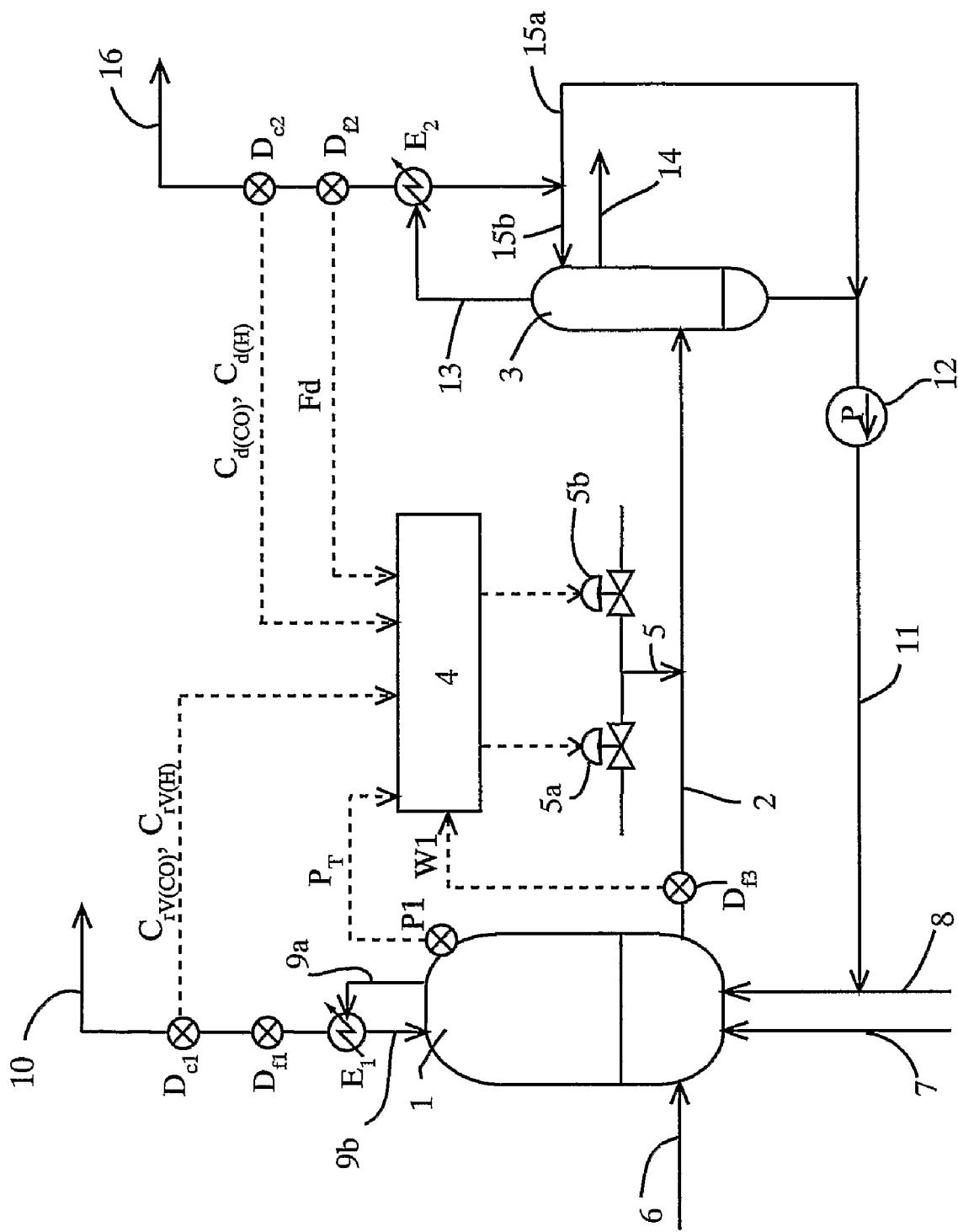
FIG. 1 is a flow diagram for explaining a process for producing a carboxylic acid according to the present invention.

The present invention shall now be described in detail with reference if necessary to the attached drawings. FIG. 1 is a flow diagram for explaining a process for producing a carboxylic acid according to the present invention.

This embodiment shows a process for producing (or purifying) acetic acid from a reaction mixture formed by a continuous carbonylation reaction of methanol and carbon monoxide in the presence of a carbonylation catalyst system comprising a rhodium catalyst and a co-catalyst (lithium iodide and methyl iodide), and a limited amount of water.

The process comprises a reaction system (a reactor) 1 for carrying out the above-mentioned carbonylation reaction of methanol; a flash distillation column (a catalyst-separation column) 3 for separating a higher-boiling component (e.g., mainly the rhodium catalyst and lithium iodide) and a lower-boiling component (e.g., acetic acid) from the reaction mixture (liquid reaction mixture or reaction fluid), the reaction mixture being continuously withdrawn from the reaction system 1 and fed or introduced through a feed line 2; a control unit (control apparatus) 4 for calculating data regarding a concentration of carbon monoxide and that of hydrogen in a liquid phase (liquid reaction mixture or reaction fluid) of the reaction system 1, and indirectly controlling the concentration of carbon monoxide and that of hydrogen based on the calculated values; a valve (magnetic valve) 5a for feeding carbon monoxide to the feed line 2 while controlling the flow rate of carbon monoxide based on a signal from the control unit 4; and a valve (magnetic valve) 5b for feeding hydrogen to the feed line 2 while controlling the flow rate of hydrogen based on a signal from the control unit 4. In the control unit 4, based on concentration data ($C_{rV(CO)}$ and $C_{rV(H)}$) of carbon monoxide and hydrogen discharged from the reaction system 1, a flow rate data ($F_d$) of a gas mixture containing carbon monoxide and hydrogen discharged from the distillation column 3, concentration data ($C_{d(CO)}$ and $C_{d(H)}$) of each gas component (CO, $H_2$) discharged from the distillation column 3, and feed rate data of the reaction fluid from the reaction system 1 to the distillation column 3 (amount of bottom solution, W1), each amount of carbon monoxide and hydrogen contained in the fluid, that is, a concentration data ($C_{rL(CO)}$) of carbon monoxide and a concentration data ($C_{rL(H)}$) of hydrogen dissolved in the liquid phase of the reaction system 1, are calculated. Then, the control unit 4 indirectly controls each of concentrations of carbon monoxide and hydrogen dissolved in the liquid phase of the reaction system, respectively, by driving or controlling each of the valves (magnetic valves) 5a and 5b based on data regarding size between thus calculated concentration data and pre-set reference (or standard) values.

More specifically, to the reactor 1, methanol as a liquid component is continuously fed at a predetermined rate through a feed line 6, and carbon monoxide as a gaseous reaction component is continuously fed through a feed line 7. Moreover, to the reactor 1, water and a catalyst mixture (a catalyst liquid) containing a carbonylation catalyst system [a catalyst system comprising a main catalyst component (e.g., a rhodium catalyst) and a co-catalyst (e.g., lithium iodide and methyl iodide)] may be fed through a feed line 8. Further, a fraction (e.g., in the form of a liquid) containing a lower-boiling component and/or a higher-boiling component from a succeeding step(s) (for example, a distillation column for purifying acetic acid) may be fed to the reactor 1 through the feed line 8. Then, in the reactor 1, a liquid-phase reaction system containing the reaction components and the higher-boiling component (s) such as the metal catalyst component (the rhodium catalyst and lithium iodide) is in equilibrium with a gas phase system comprising carbon monoxide, hydrogen produced by the reaction, and a vaporized lower-boiling component(s) (methyl iodide, produced acetic acid, and methyl acetate). Incidentally, to the reactor 1, if necessary, hydrogen may be fed in order to enhance the catalyst activity. Such hydrogen may be fed together with carbon monoxide through the feed line 7, or may be separately fed through another feed line (not shown). Incidentally, since the reaction system is an exothermic reaction system accompanied by generation of heat, the reactor 1 may be equipped with a heat-removing unit or a cooling unit (e.g., a jacket) for controlling the reaction temperature.

Moreover, the lower-boiling component(s), that is, a waste gas component(s) (waste gas stream) containing carbon monoxide, hydrogen and others, is discharged from the top of the reactor 1 through a discharge line 9a, introduced into a heat exchanger $E_1$, cooled, and separated into a liquid component(s) (containing methyl acetate, methyl iodide, water, acetic acid, and others) and a gas component(s) (containing carbon monoxide and hydrogen), and the gas component(s) is discharged through a discharge line 10 and the liquid component(s) is recycled to the reactor 1 through a recycle line 9b. In the passage of the gas component, that is, in the discharge line 10, a detector (a flowmeter) $D_{f1}$ for detecting the total flow rate data $F_r$ of a gas component containing carbon monoxide and hydrogen contained in the gas phase within the reactor, and a detector (an analyzer) $D_{c1}$ for detecting concentration data ($C_{rV(CO)}$ and $C_{rV(H)}$) of carbon monoxide and hydrogen, contained in the gas phase within the reactor 1 are disposed. The detection data ($C_{rV(CO)}$ and $C_{rV(H)}$) from the analyzer $D_{c1}$ are continuously fed to the control unit 4. Incidentally, the reactor 1 is equipped with a pressure gage P1 for measuring an inner pressure (total pressure) data $P_T$ of the reactor, and the total pressure data $P_T$ from the pressure gage is also continuously fed to the control unit 4. Moreover, if necessary, the total flow rate data $F_r$ from the flowmeter $D_{f1}$ may be provided to the control unit 4.

Incidentally, in the reaction mixture (crude reaction liquid or fluid) produced in the reactor 1, is contained the metal catalyst component (the rhodium catalyst, and lithium iodide as a co-catalyst), acetic acid, methyl iodide as a co-catalyst, methyl acetate and water which are products obtained by a reaction between acetic acid and methanol, and in addition, as impurities, a lower-boiling impurity (e.g., acetaldehyde as a precursor of acetic acid) whose boiling point is lower than that of acetic acid and a higher-boiling impurity (e.g., propionic acid) whose boiling point is higher than that of acetic acid, and others.

In order to separate acetic acid from the above-mentioned reaction mixture, the reaction mixture is introduced or fed to the distillation column 3 through the feed line 2 equipped with a valve (not shown) while a part of the reaction mixture is continuously withdrawn from the reactor 1. The feed line 2 is equipped with a detector (a flowmeter) $D_{f3}$ for measuring the flow rate data W1 of the reaction mixture fed from the reactor 1, and the detection data from the flowmeter $D_{f3}$ is continuously fed to the control unit 4.

Moreover, in the distillation column 3, a higher-boiling component (or higher-boiling components) (mainly, a metal catalyst component(s) such as the rhodium catalyst and lithium iodide, and others) and a lower-boiling component (or lower-boiling components) (mainly, acetic acid which is a product and also acts as a reaction solvent, methyl acetate, methyl iodide, water, and others) are separated from the reaction mixture, and the higher-boiling component is withdrawn from the bottom of the column, and the lower-boiling component is distilled off through a distillation line 14 from the upper plate (or stage) of the distillation column. Moreover, from the top of the distillation column 3, a gas component (offgas) mainly containing carbon monoxide and hydrogen is discharged through a discharge line 13. Incidentally, the higher-boiling component also contains methyl iodide, methyl acetate, water and acetic acid which remain without vaporization, in addition to the metal catalyst component. Incidentally, further generation of by-products or decrease in the catalyst activity may be inhibited by lowering the inner temperature and/or pressure of the distillation column 3 than the inner temperature and pressure of the reactor 1, respectively.

The gas component discharged from the top of the distillation column 3 is introduced into a heat exchanger $E_2$, cooled, and separated into a liquid component and a gas component. The liquid component (containing methyl acetate, methyl iodide, acetic acid, water, and others) is recycled to the reactor 1 and/or the distillation column 3 through a recycle line 15a (and a recycle line 11) and/or 15b. The gas component (containing carbon monoxide and hydrogen, and others) is discharged through a discharge line 16. Incidentally, from the separated liquid component, if necessary, an aldehyde may be removed by an aldehyde separation column or others, and useful components (e.g., methyl iodide, and methyl acetate) may be recycled to the reactor or the distillation column.

Moreover, the discharge line 16 for discharging the gas component is equipped with a detector (a flowmeter) $D_{f2}$ for measuring the flow rate data $F_d$ of the gas component, and a detector (an analyzer) $D_{c2}$ for measuring concentration data $C_{d(CO)}$ and $C_{d(H)}$ of carbon monoxide and hydrogen contained in a discharged gas. The flow rate data $F_d$ from the flowmeter $D_{f2}$, and the concentration data $C_{d(CO)}$ and $C_{d(H)}$ from the analyzer $D_{c2}$ are continuously fed to the control unit 4.

Incidentally, continuous feeding of the data from each of the detector or the pressure gage mentioned above to the control unit 4 is not necessary required. The data may be fed to the control unit periodically (e.g., periodically with short intervals) or intermittently.

Moreover, the gas component discharged through the discharge line 10 and/or 16 contains large quantities of carbon monoxide and hydrogen, and if necessary may be recycled to the reactor 1, for example, through the feed line 7 (not shown), or utilized as a source of supply for carbon monoxide and hydrogen to be introduced into the feed line 2 through the feed line 5 (not shown). Incidentally, in order to recover the gas component (e.g., carbon monoxide and/or hydrogen), a conventional recovery apparatus, e.g., an absorber (e.g., PSA) may be used.

On the other hand, the lower-boiling component separated from the distillation column 3 through the distillation line 14 contains a large quantity of acetic acid which is a product, and such a lower-boiling component may be recovered as a finished product as it is. Moreover, if necessary, acetic acid with a high purity may be recovered by subjecting the lower-boiling component to a conventional separation or purification step (e.g., a distillation step) for separating from other components (e.g., by-products such as acetaldehyde and propionic acid, water, methyl acetate, and methyl iodide).

The higher-boiling catalyst component (circulating catalyst solution) is separated by the distillation column 3, then recycled (circulated) to the reaction system (the reactor 1) through the recycle line 11. In the recycle line 11, the bottom solution from the distillation column 3 may be recycled to the reactor 1, if necessary, by pressurizing with a pressure pump 12. The bottom solution from the distillation column 3 may be recycled to the reactor 1 through the recycle line 11 and the catalyst feed line 8 as shown in FIG. 1, or directly fed to the reactor 1 through a recycle line (not shown) which directly leads to the reactor without passing through the feed line 8.

Figure 2:
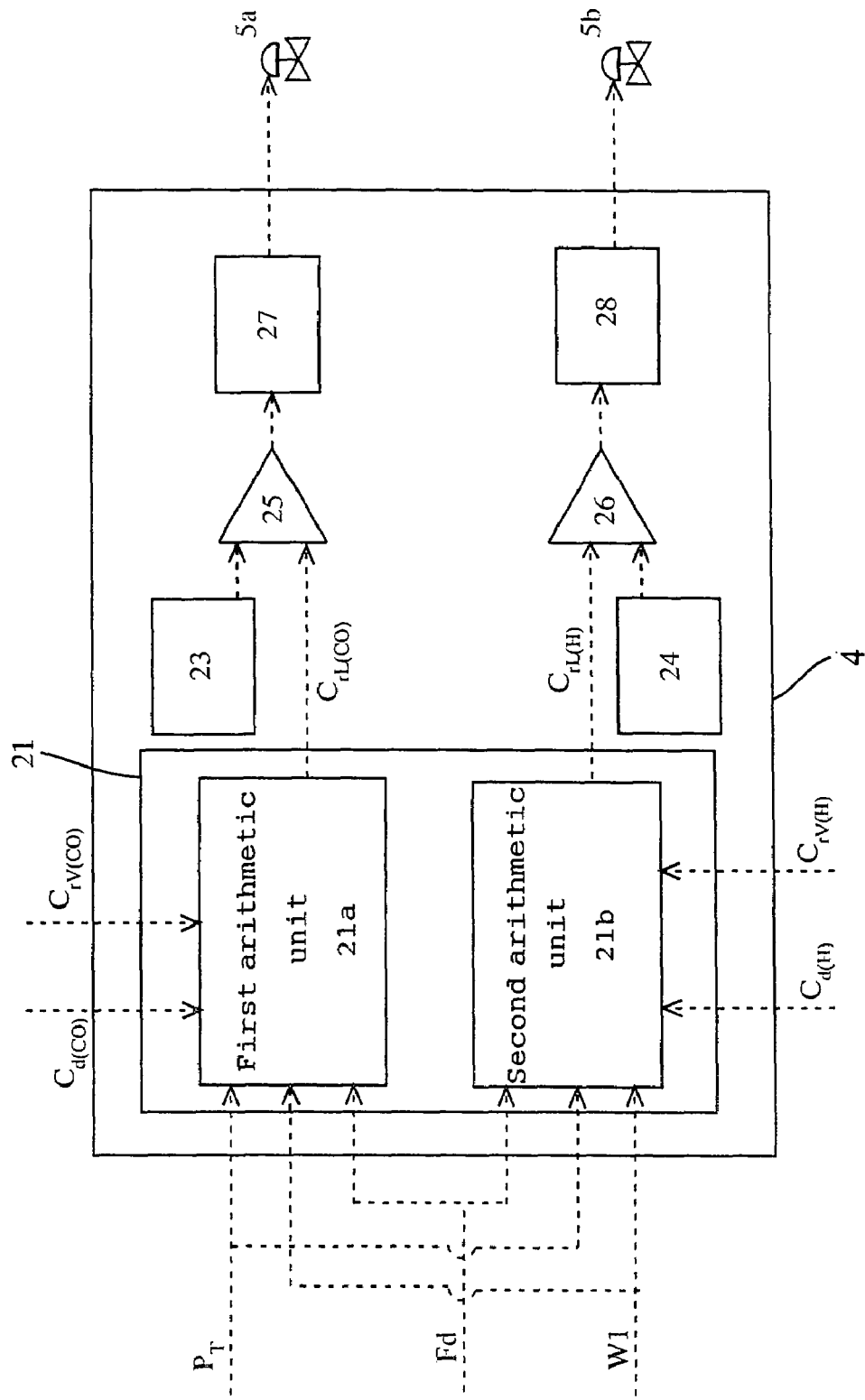
FIG. 2 is a block diagram for explaining a control unit in FIG. 1.

FIG. 2 is a block diagram for explaining the control unit 4 of FIG. 1. As described above, to the control unit 4, the concentration data ($C_{rV(CO)}$, $C_{rV(H)}$) from the analyzer $D_{c1}$ provided in the discharge line 10, the flow rate data ($F_d$) and the concentration data ($C_{d(CO)}$, $C_{d(H)}$) from the flowmeter $D_{f2}$ and the analyzer $D_{c2}$ provided in the discharge line 16, the feed (or flow) rate data (W1) from the flowmeter $D_{f3}$ provided in the feed line 2 leading to the distillation column 3 from the reactor 1, and in addition, the total pressure data $P_T$ from the pressure gage P1 are fed.

Hereinafter, flow of each data up to drive the valves 5a, 5b is explained.

In the embodiment of FIG. 2, the control unit 4 comprises an arithmetic system 21 for calculating each concentration data of carbon monoxide and hydrogen contained in the liquid phase of the reactor 1 mainly based on the above-mentioned each data, setting units 23 and 24 for setting reference values to be compared with each of the concentration data calculated by the arithmetic system 21, comparing units 25 and 26 for comparing the concentration data from the arithmetic system 21 with the reference values from the setting units 23 and 24, respectively, and driving units 27 and 28 for driving magnetic valves 5a and 5b in association with comparison results in the comparing unit (that is, the size between the concentration data and each of the reference values), respectively. Then, by opening or closing the magnetic valve 5a and/or 5b based on signals from driving units 27 and 28, feeding of carbon monoxide and/or hydrogen to the feed line 2 is controlled.

More specifically, the arithmetic system 21 comprises a first arithmetic unit 21a for receiving data (flow rate data, concentration data) mainly regarding carbon monoxide and calculating the concentration data of carbon monoxide contained in the liquid phase of the reactor 1, and a second arithmetic unit 21b for receiving data (flow rate data, concentration data) mainly regarding hydrogen and calculating the concentration data of hydrogen contained in the liquid phase of the reactor 1. To both of the first and second arithmetic units, in addition to the data regarding carbon monoxide or hydrogen, the flow rate data $F_d$ of the gas component in the distillation column 3, the total pressure data $P_T$ of the reactor 1, and the feed rate data W1 of the reaction fluid in the feed line 2 are fed, and a calculated value ($P_o$) of a vapor pressure of the organic component as the lower-boiling component in the reactor 1 is set in advance. Incidentally, for the calculation of the vapor pressure data $P_O$, may be employed an arithmetic system (not shown) for calculating the vapor pressure data $P_O$ based on the total pressure data, the temperature data and the reaction fluid formulation data of the reaction system (output value(s) of an automatic analyzer).

Incidentally, the above-mentioned reaction fluid formulation data is often given by sampling the reaction fluid by an automatic analyzer (e.g., a conventional analyzer, e.g., a gas chromatography, an infrared moisture balance, and FT-IR) at a constant rate or continuously, and converting automatically analyzed concentrations of methyl iodide, methyl acetate, water, acetic acid, and others into an electronic signal(s).

In the first arithmetic unit 21a, based on the calculated data $P_O$ of the vapor pressure of the organic component, the total pressure data $P_T$ of the reactor 1, and the concentration data $C_{rV(CO)}$ from the detector $D_{c1}$, the partial pressure data of carbon monoxide ($P_{CO}$) in the gas phase system of the reactor 1 is calculated in accordance with the following formula (1):

$$P_{CO}=(P_T-P_O)\times C_{rV(CO)} \quad (1)$$

wherein $P_T$, $P_O$, and $C_{rV(CO)}$ have the same meanings as defined above.

Further, in the first arithmetic unit 21a, based on the flow rate data $F_d$ of the gas component in the distillation column 3 provided from the flowmeter $D_{f2}$, the concentration data $C_{d(CO)}$ of carbon monoxide in the gas component in the distillation column 3, the partial pressure data $P_{CO}$ of carbon monoxide in the gas phase of the reaction system 1, and the feed rate data W1 of the reaction fluid, the concentration data $C_{rL(CO)}$ of carbon monoxide in the liquid phase (reaction fluid) in the reactor 1 is calculated in accordance with the following formula (2). The first arithmetic unit provides the calculated concentration data $C_{rL(CO)}$ of carbon monoxide in the liquid phase to the comparing unit 25.

$$C_{rL(CO)}=(F_d\times C_{d(CO)})/P_{CO}/W1 \quad (2)$$

In the formula, $F_d$, $C_{d(CO)}$, $P_{CO}$, and W1 have the same meanings as defined above.

In the comparing unit 25, the concentration data $C_{rL(CO)}$ of carbon monoxide provided from the first arithmetic unit 21a is compared with the reference value preset in the setting unit 23 (for example, data corresponding to "2 mmol relative to 1 kilogram of the liquid phase by weight per 1 MPa of the carbon monoxide partial pressure in the reaction system"), and data regarding the size between the concentration data and the reference value is fed to the driving unit 27. Thereafter, the driving unit 27 controls opening and closing of the magnetic valve 5a based on the data provided from the comparing unit 25, and adjusts the concentration of carbon monoxide in the reaction fluid passing through the feed line 2, as a result, the concentration of carbon monoxide in the reactor 1. That is, when the concentration data $C_{rL(CO)}$ is not less than the reference value in the comparing unit 25, the driving unit 27 makes the magnetic valve 5a close and stops supply of carbon monoxide to the feed line 2. On the other hand, when the concentration data is smaller than the reference value, the driving unit 27 makes the magnetic valve 5a open and supplies carbon monoxide to the feed line 2.

The data flow from the first arithmetic unit 21a to the magnetic valve 5a through the comparing unit 25 and the driving unit 27 is the same as a data flow in the system for processing the data regarding hydrogen from the second arithmetic unit 21b to the magnetic valve 5b through the comparing unit 26 and the driving unit 28. That is, in the second arithmetic unit 21b, as is the case with the first arithmetic unit 21a, the concentration data $C_{rL(H)}$ of hydrogen in the liquid phase in the reactor 1 based on the data regarding hydrogen is calculated. Namely, in the second arithmetic unit 21b, based on the vapor pressure data $P_O$, the total pressure data $P_T$, and the concentration data $C_{rV(H)}$ of hydrogen in the gas phase of the reactor 1, the partial pressure data ($P_H$) of hydrogen is calculated in accordance with the following formula (3):

$$P_H=(P_T-P_O)\times C_{rV(H)} \quad (3)$$

wherein $P_T$, $P_O$, and $C_{rV(H)}$ have the same meanings as defined above.

Then, in the second arithmetic unit 21b, as is the case with the concentration $C_{rL(CO)}$ of carbon monoxide, the concentration $C_{rL(H)}$ of hydrogen in the liquid phase (reaction fluid) in the reactor 1 is calculated based on the following formula (4), and the calculated data $C_{rL(H)}$ is fed to the comparing unit 26.

$$C_{rL(H)}=(F_d\times C_{d(H)})/P_H/W1 \quad (4)$$

In the formula, $F_d$, $C_{d(H)}$, $P_H$, and W1 have the same meanings as defined above.

In the comparing unit 26, the calculated data $C_{rL(H)}$ fed from the second arithmetic unit 21b is compared with the reference value provided from the setting unit 24 (e.g., data corresponding to 50 mmol relative to 1 kilogram of the liquid phase by weight per 1 MPa of the hydrogen partial pressure in the reaction system), and data regarding the size between the both is provided to the driving unit 28. Thereafter, the driving unit 28 adjusts the concentration of hydrogen in the reaction fluid passing through the feed line 2, as a result, the concentration of hydrogen in the reaction fluid in the reactor 1, by controlling opening and closing of the magnetic valve 5b based on the data regarding the size provided from the comparing unit 24.

Incidentally, both of a series of units (the first arithmetic unit 21a, the setting unit 23, the comparing unit 25, the driving unit 27, and the magnetic valve 5a) for controlling supply of carbon monoxide, and a series of units (the second arithmetic unit 21b, the setting unit 24, the comparing unit 26, the driving unit 28, and the magnetic valve 5b) for controlling supply of hydrogen are not necessarily required. Either one of the series of units may be provided. Moreover, supply of gas from the magnetic valves 5a and 5b is not necessarily conducted through the same feed line 5, and carbon monoxide and hydrogen may be fed to the feed line 2 by passing through separate feed lines, respectively. Further, each of carbon monoxide and hydrogen may be fed to the feed line 2 as pure gas, or may be used by diluting with an inactive gas (e.g., nitrogen, helium, and carbon dioxide). Furthermore, the discharged gas from the reactor (that is, the discharge line 10) or the succeeding step (e.g., the distillation column 3 (that is, the discharge line 16)) may be recycled.

Figure 3:
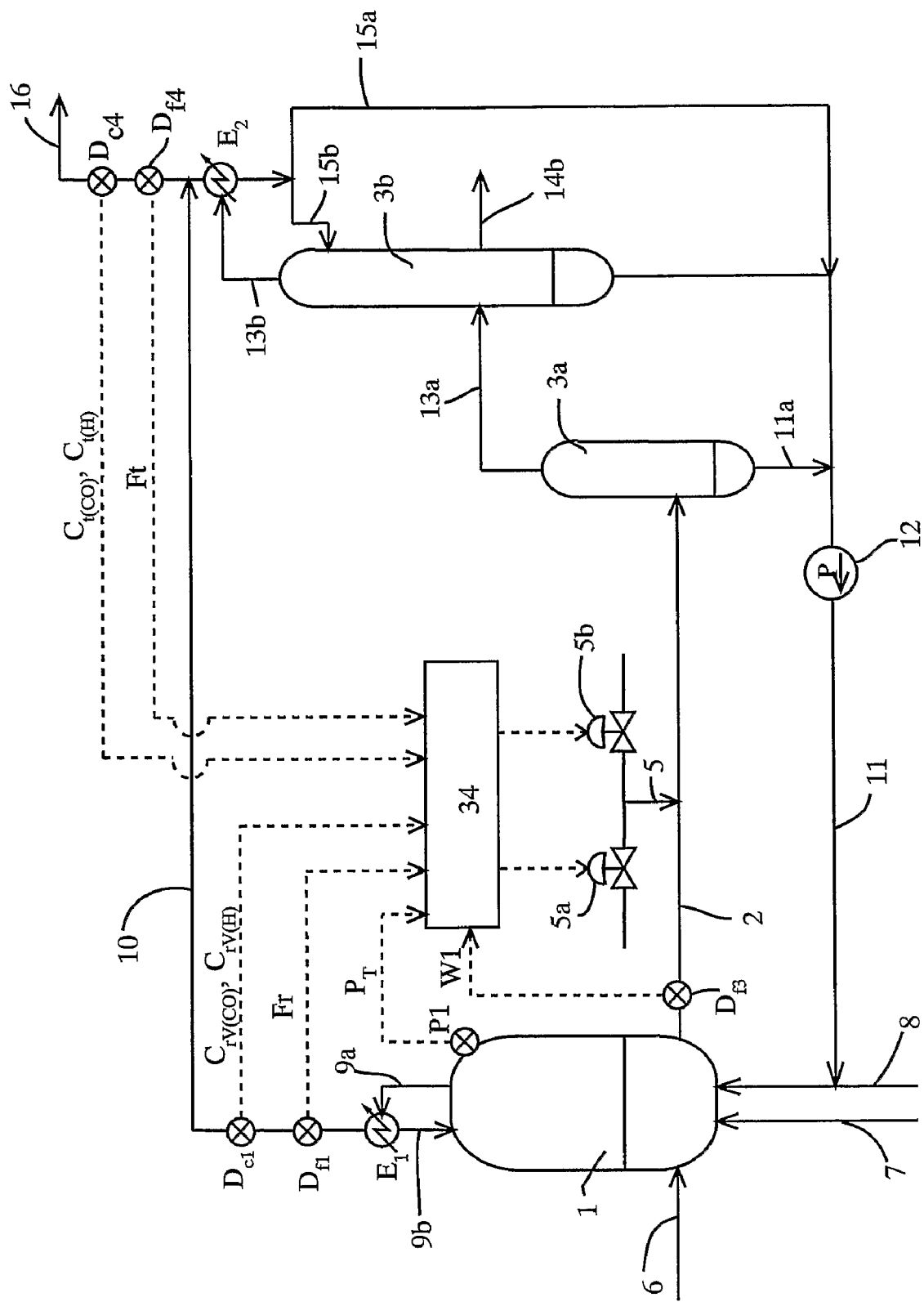
FIG. 3 is a flow diagram for explaining another process for producing a carboxylic acid according to the present invention.

FIG. 3 is a flow diagram for explaining another embodiment of a process for producing a carboxylic acid according to the present invention. In the embodiment of FIG. 3, compared with that of FIG. 1, the reaction mixture from the reactor 1 is purified with two distillation columns 3a (catalyst-separation column) and 3b (carboxylic acid-purification column), a waste gas stream from the reactor 1 (that is, from the discharge line 10) is joined into a waste gas stream from the distillation column 3b. Then, without detecting the flow rate data ($F_d$) of the waste gas from the distillation column and the concentration data ($C_{d(CO)}$, $C_{d(H)}$) of each gas, the flow rate data ($F_t$) and the concentration data ($C_{t(CO)}$, $C_{t(H)}$) of each gas component with respect to a waste gas from the reactor 1 and the distillation columns (3a, 3b) are detected by a flowmeter $D_{f4}$ and an analyzer $D_{c4}$, respectively, which are provided with a passage of the joined waste gas stream. Thus detected data are fed to the control unit 34.

That is, the process of FIG. 3 comprises the reactor 1 for carrying out the carbonylation reaction; the flash distillation column (catalyst-separation column) 3a for separating a higher-boiling component(s) (e.g., a catalyst component(s)) from a reaction mixture obtained from the reactor 1; the distillation column (carboxylic acid-purification column or higher-boiling component-recovery column) 3b for further separating a higher-boiling impurity (or impurities) (e.g., propionic acid, and water) and a lower-boiling component(s) (containing a purified acetic acid) from a lower-boiling component(s) introduced from the distillation column 3a; the control unit 34 for calculating data regarding carbon monoxide concentration and hydrogen concentration in the liquid phase of the reactor 1, and indirectly controlling the carbon monoxide concentration and the hydrogen concentration in the liquid phase based on the calculated values; and the magnetic valves 5a and 5b for feeding carbon monoxide and hydrogen to the feed line 2 while controlling each of the flow rates of carbon monoxide and hydrogen based on signals from the control unit 34.

In the embodiment of FIG. 3, the reaction mixture from the reactor 1 is firstly introduced into the catalyst-separation column 3a. In the catalyst-separation column 3a, the metal catalyst components such as the rhodium catalyst and lithium iodide are mainly separated as a higher-boiling component from the column bottom and withdrawn through a bottom line 11a, and a lower-boiling component is distilled off from the top of the column. The higher-boiling component from the distillation column 3a may be recycled to the reactor 1 through the recycle line 11 and the feed line 8. The lower-boiling component from the distillation column 3a is introduced into the carboxylic acid-purification column (the higher-boiling component-recovery column) 3b through a feed line 13a. In the carboxylic acid-purification column 3b, a higher-boiling component mainly containing propionic acid is separated from the column bottom, a lower-boiling component containing acetic acid is distilled off by side cut through a distillation line 14b, and a gas component(s) (waste gas component(s)) containing carbon monoxide and hydrogen, in addition methyl acetate, methyl iodide, and others, is separated from the top of the column. The higher-boiling component from the distillation column 3b may be recycled to the reactor 1 through the recycle line 11 and the feed line 8. Moreover, the waste gas component from the distillation column 3b is introduced into the heat exchanger $E_2$, cooled, and separated into a liquid component and a gas component. The separated liquid component contains methyl iodide, methyl acetate, acetaldehyde, water, and others, and is recycled to the reactor 1 and/or the distillation column 3b through the recycle line 15a and/or 15b. The separated gas component is discharged through the discharge line 16. Incidentally, if necessary, from the separated liquid component, aldehyde may be removed by an aldehyde separation column or other means, and useful components (e.g., methyl iodide, and methyl acetate) may be recycled to the reactor and/or the distillation column.

On the other hand, the gas component which is discharged from the top of the reactor 1 and separated by the heat exchanger $E_1$ as is the case with the embodiment of FIG. 1 is joined together with, through the discharge line (feed line) 10, a gas component in a waste gas stream discharged from the distillation column 3b (that is, a gas component from the heat exchanger $E_2$), and is discharged through the discharge line 16. In the embodiment of FIG. 3, the passage of the gas component from the reactor 1 (discharge line 10) is equipped with the flowmeter $D_{f1}$ and the analyzer $D_{c1}$. The flowmeter $D_{f1}$ detects the total flow rate data $F_r$ of carbon monoxide, hydrogen and others contained in the gas phase in the reactor 1, and the analyzer $D_{c1}$ detects the concentration data $C_{rV(CO)}$ and $C_{rV(H)}$ of carbon monoxide and hydrogen contained in the gas phase in the reactor 1. In addition, these flowmeter and analyzer provide these data to the control unit 34. Moreover, the discharge line 16 is equipped with the flowmeter $D_{f4}$ and the analyzer $D_{c4}$ in the lower stream of the junction of the gas component from the reactor 1 and the gas component from the distillation column 3b (that is, in the passage of the joined waste gas stream). The total amount of carbon monoxide and hydrogen in the reactor 1 is detected as a flow rate data $F_t$ by the flowmeter $D_{f4}$, and the total concentration data ($C_{t(CO)}$, $C_{t(H)}$) of carbon monoxide and hydrogen in the reactor 1 is detected by the analyzer $D_{c4}$. Then, these data are fed to the control unit 34.

Incidentally, the gas component discharged through the discharge line 16 contains large quantities of carbon monoxide and hydrogen, and if necessary, may be, for example, recycled (not shown) to the reactor 1 through the feed line 7, or may be utilized as a source of supply of carbon monoxide and hydrogen (not shown) to be introduced into the feed line 2 through the feed line 5. Incidentally, for recovering the gas component (e.g., carbon monoxide and/or hydrogen), a conventional recovery apparatus, for example, an absorber (e.g., PSA) may be employed.

Figure 4:
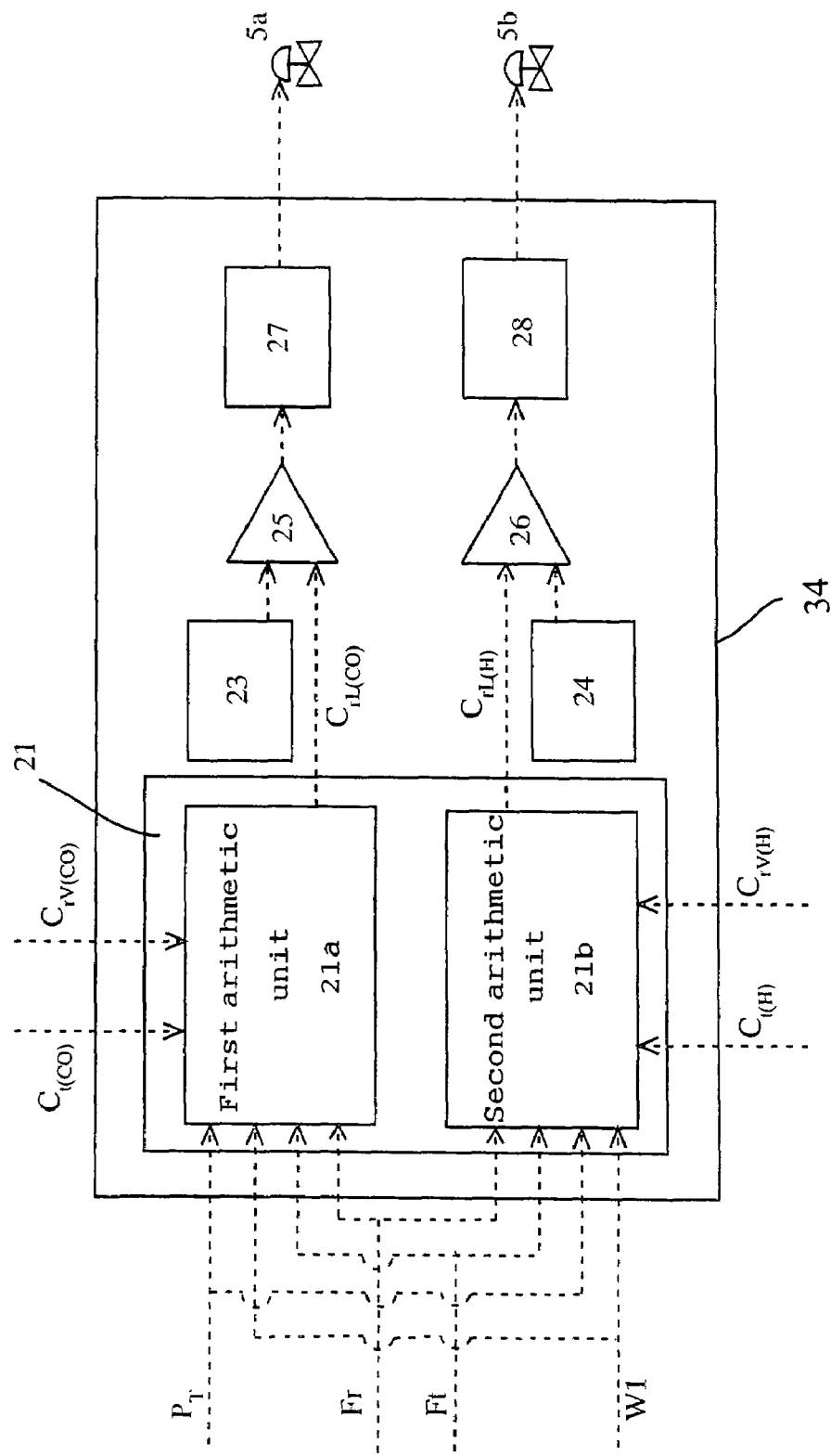
FIG. 4 is a block diagram for explaining a control unit in FIG. 3.

FIG. 4 is a block diagram for explaining the control unit 34 of FIG. 3. As describe above, to the control unit 34 are provided the flow rate data ($F_r$) and the concentration data ($C_{rV(CO)}$, $C_{rV(H)}$) from the flowmeter $D_{f1}$ and the analyzer $D_{c1}$ regarding the waste gas component (that is, carbon monoxide and hydrogen in the gas phase) from the reaction system 1, the flow rate data (the data $F_t$ of the total offgas amount) and the concentration data ($C_{t(CO)}$, $C_{t(H)}$) from the flowmeter $D_{f4}$ and the analyzer $D_{c4}$ regarding the waste gas component from the reaction system 1 and the waste gas component from the distillation column 3b (that is, carbon monoxide and hydrogen in the liquid phase of the reaction system), the flow rate data (W1) from the flowmeter $D_{f3}$ equipped with the feed line 2 leading to the distillation column 3a from the reaction system 1, and the total pressure data $P_T$ from the pressure gage P1.

In the embodiment of FIG. 4, an arithmetic system 21 for calculating each of the concentration data of carbon monoxide and hydrogen contained in the liquid phase of the reactor 1 comprises a first arithmetic unit 21a for receiving the data (flow rate data, concentration data) mainly regarding carbon monoxide and calculating the concentration data of the carbon monoxide contained in the liquid phase of the reactor 1, and a second arithmetic unit 21b for receiving the data (flow rate data, concentration data) mainly regarding hydrogen and calculating the concentration data of the hydrogen contained in the liquid phase of the reactor 1. Then, to each of the first and second arithmetic units, the total flow rate date $F_t$ from the flowmeter $D_{f4}$, the flow rate data $F_r$ regarding the gas phase of the reactor 1 from the flowmeter $D_{f1}$, the total pressure data $P_T$ of the reactor 1, and the feed rate data W1 of the reaction fluid in the feed line 2 are fed in addition to the data regarding carbon monoxide or hydrogen. Additionally, to both of these units, a calculated value ($P_O$) of a vapor pressure of the organic component which is the lower-boiling component in the reactor 1 is set in advance. Incidentally, the vapor pressure data $P_O$ may be calculated by the same means as FIG. 1.

In the embodiment of FIG. 4, the flow rate data $F_r$ in the gas phase of the reaction system 1, and the total flow rate data $F_t$ are provided from the flowmeter $D_{f1}$ and the flow meter $D_{f4}$, respectively. The partial pressure data $P_{CO}$ of carbon monoxide and the partial pressure data $P_H$ of hydrogen in the gas phase system in the reactor 1 are calculated in the same manner as the embodiment of FIG. 2 except that not the concentration data $C_{d(CO)}$ and $C_{d(H)}$ in the distillation column but the total concentration data $C_{t(CO)}$ and $C_{t(H)}$ from the reactor and the distillation column are directly provided to the first and second arithmetic units 21a and 21b from the analyzer $D_{c2}$. Then, the carbon monoxide concentration data $C_{rL(CO)}$ and the hydrogen concentration data $C_{rL(H)}$ in the liquid phase of the reactor 1 are calculated in accordance with the following formulae (5) and (6), respectively, based on the following data: the total flow rate data $F_t$, the total concentration data $C_{t(CO)}$ and $C_{t(H)}$ of carbon monoxide and hydrogen, the flow rate data $F_r$ from the reaction system, the concentration data $C_{rV(CO)}$ and $C_{rV(H)}$ of carbon monoxide and hydrogen from the reaction system, each partial pressure data $P_{CO}$ and $P_H$ of carbon monoxide and hydrogen, and the feed rate data W1 of the reaction fluid. The first and second arithmetic units provide the calculated concentration data $C_{rL(CO)}$ and $C_{rL(H)}$ of carbon monoxide and hydrogen in the liquid phase to the comparing units 25 and 26, respectively.

$$C_{rL(CO)}=[F_r\times C_{t(CO)}-F_r\times C_{rV(CO)}]/P_{CO}/W1 \quad (5)$$

$$C_{rL(H)}=[F_r\times C_{t(H)}-F_r\times C_{rV(H)}]/P_H/W1 \quad (6)$$

In the formulae, $F_t$, $C_{t(CO)}$, $F_r$, $C_{rV(CO)}$, $P_{CO}$, $C_{t(H)}$, $C_{rV(H)}$, $P_H$, and W1 have the same meanings as defined above.

Then, based on these concentration data, in the similar flow as in the embodiment of FIG. 2, the opening and closing of the magnetic valve 5a and/or 5b are controlled, and the carbon monoxide concentration and/or the hydrogen concentration in the reaction fluid passing through the feed line 2, as a result, the carbon monoxide concentration and/or the hydrogen concentration in the reactor 1 are regulated.

Incidentally, in the embodiment of FIG. 1, in the same manner as in the embodiment of FIG. 3, the total flow rate data $F_t$ of the offgas component, and the total concentration data $C_{t(CO)}$ and $C_{t(H)}$ of each gas may be detected by joining the discharge line 10 together with the discharge line 16, and the concentration of carbon monoxide and/or hydrogen in the liquid phase may be regulated in accordance with the block diagram of FIG. 4. Moreover, in the embodiment of FIG. 1, the concentration of each gas in the liquid phase in accordance with the block diagram of FIG. 4 may be regulated by feeding, to the control unit 4, the total flow rate data $F_r$ of the offgas component from the reactor, and the flow rate data $F_d$ of the off gas component from the distillation column, separately calculating $F_t$ based on the flow rate data with the use of the arithmetic unit, and calculating the concentration of each gas in the liquid phase of the reaction system based on the formulae (5) and (6). Further, in the embodiment of FIG. 3, in the same manner as in the embodiment of FIG. 1, the concentration of each gas in the liquid phase of the reaction system may be regulated in accordance with the block diagram of FIG. 2 by separately measuring the flow rate data $F_d$ and the concentration data of each gas from the distillation column, and the concentration data of each gas from the reaction system without joining the discharge line 10 together with the discharge line 16.

In this manner, according to the present invention, even when the water content of the reaction system is low, deactivation or precipitation of the catalyst can be inhibited by keeping the carbon monoxide concentration and/or the hydrogen concentration of the reaction system (in the liquid phase) to a predetermined value. Thereby, deterioration of the reaction rate can be also inhibited. Moreover, since the present invention ensures to reduce the water content of the reaction system while inhibiting deterioration of the reaction rate, the amount of by-products can be decreased. Further, since decrease of the reaction rate is inhibited without enhancing the hydrogen partial pressure in the reaction system reactor needlessly, side reactions accompanying increase of the hydrogen partial pressure can be prevented, and therefore, generation of by-products can be inhibited.

The production process of the present invention is not particularly limited to the above-mentioned carbonylation of methanol, and is applicable to carbonylation reactions of various alcohols or derivatives thereof.

(Carbonylation Reaction System)

In the reaction system, an alcohol or a derivative thereof (a reactive derivative such as an ester, an ether, or a halide) is carbonylated with carbon monoxide. Examples of the alcohol used for the carbonylation reaction may include an alcohol having a carbon number of "n", for example, an aliphatic alcohol [for example, an alkanol such as methanol, ethanol, propanol, isopropanol, butanol, pentanol, or hexanol (e.g., a $C_{1-10}$alkanol)], an alicyclic alcohol [for example, a cycloalkanol such as cyclohexanol, or cyclooctanol (e.g., a $C_{3-10}$cycloalkanol)], and an aromatic alcohol [for example, an aryl alcohol such as phenol (e.g., a $C_{6-10}$aryl alcohol (such as a phenol compound)); and an aralkyl alcohol such as benzyl alcohol, or phenethyl alcohol (e.g., a $C_{6-10}$aryl-$C_{1-4}$alkanol)]. The carbon number "n" is about 1 to 14, preferably about 1 to 10, and more preferably about 1 to 6. Among the above-mentioned alcohols, the aliphatic alcohol is preferred. The carbon number "n" of the aliphatic alcohol is, for example, about 1 to 6, preferably about 1 to 4, and particularly about 1 to 3.

Among the alcohol derivatives, the ester may include an ester of a produced carboxylic acid with an alcohol as a raw material, for example, a $C_{1-6}$alkyl ester of a $C_{2-6}$ carboxylic acid such as methyl acetate, or ethyl propionate. The ether may include an ether corresponding to an alcohol as a raw material, for example, a $diC_{1-6}$alkyl ether such as methyl ether, ethyl ether, propyl ether, isopropyl ether, or butyl ether. Moreover, as the halide, there may be mentioned a halide corresponding to the alcohol, such as methyl iodide (e.g., an alkyl halide such as an alkyl iodide). Further, if necessary, as the alcohol, a polyhydric alcohol, for example, an alkylene glycol such as ethylene glycol, propylene glycol or butanediol, or a derivative thereof (e.g., an ester, a halide, and an ether) may be employed.

The alcohol or the derivative thereof may be used singly or in combination.

In the preferred liquid phase reaction system, a carboxylic acid having a carbon number of "n+1" or a derivative thereof (e.g., a carboxylic acid anhydride) may be obtained by using an alcohol having a carbon number of "n", preferably a $C_{1-4}$alcohol or a derivative thereof (e.g., methanol, methyl acetate, methyl iodide, and dimethyl ether) as a liquid reaction component. In particular, the preferred reaction system is a system in which acetic acid or a derivative thereof is produced by allowing at least one member selected from the group consisting of methanol, methyl acetate, and dimethyl ether (particularly, at least methanol) to react with carbon monoxide in a liquid phase reaction system in the presence of a carbonylation catalyst system.

Incidentally, the alcohol or the derivative thereof may be directly or indirectly fed to the reaction system as a fresh raw material, or may be fed to the reaction system by recycling an alcohol or a derivative thereof which is a distillate from the distillation step.

The catalyst system in the reaction system may comprise a carbonylation catalyst, and a co-catalyst or an accelerator. As the carbonylation catalyst, a higher-boiling catalyst, e.g., a metal catalyst is usually employed. The metal catalyst may include a transition metal catalyst, in particular, a metal catalyst containing a metal of the group 8 of the Periodic Table of Elements, for example, a cobalt catalyst, a rhodium catalyst, an iridium catalyst, and others. The catalyst may be a metal substance, or may be in the form of a metal oxide (including a compound oxide), a hydroxide, a halide (e.g., a chloride, a bromide, and an iodide), a carboxylic acid salt (e.g., an acetate), an inorganic acid salt (e.g., a sulfate, a nitrate, and a phosphate), a complex, or others. Such a metal catalyst may be used singly or in combination. Incidentally, as a ligand constituting the complex, there may be exemplified OH (hydroxy); an alkoxy group such as methoxy, or ethoxy group; an acyl group such as acetyl group; an alkoxycarbonyl group such as methoxycarbonyl (acetato), or ethoxycarbonyl group; acetylacetonato, cyclopentadienyl group; a halogen atom such as chlorine, bromine or iodine; CO; CN; oxygen atom; $H_2O$ (aquo); a phosphorus compound such as a phosphine; and a nitrogen-containing compound such as $NH_3$, NO, or ethylenediamine. As to the complex, a single ligand or ligands of the same or different kinds may be coordinated therein.

The preferred metal catalyst includes a rhodium catalyst and an iridium catalyst (particularly, a rhodium catalyst). Moreover, the metal catalyst is preferably used in a soluble form in the reaction fluid. Incidentally, in the case of using the rhodium catalyst, since rhodium usually exists as a complex in the reaction fluid, the catalyst is not particularly limited to a specific one as long as the catalyst is transmutable (or convertible) to a complex in the reaction fluid. Therefore, the rhodium catalyst may be in various forms. As such a rhodium catalyst, particularly a rhodium halide (e.g., bromide, and iodide) is preferred. Moreover, the catalyst can be stabilized in the reaction fluid by addition of a halide salt (e.g., an iodide salt) and/or water.

The concentration of the catalyst is, for example, about 10 to 5,000 ppm, preferably about 100 to 4,000 ppm, more preferably about 300 to 3,000 ppm, and particularly about 500 to 2,000 ppm on the basis of weight relative to the whole liquid phase. In the case where the concentration of the catalyst is too high, the catalyst (e.g., the rhodium catalyst) is changed to an insoluble component (e.g., a rhodium halide such as rhodium iodide) and precipitated, and as a result, there is a possibility that the reaction efficiency and productivity are deteriorated.

As the co-catalyst or the accelerator constituting the above-mentioned catalyst system, there may be used various halides, for example, an alkali metal halide (e.g., an iodide such as lithium iodide, potassium iodide, or sodium iodide; and a bromide such as lithium bromide, potassium bromide, or sodium bromide), a hydrogen halide (e.g., hydrogen iodide, and hydrogen bromide), an alkyl halide [e.g., an alkyl halide corresponding to an alcohol as a raw material (a $C_{1-10}$ alkyl halide, and preferably a $C_{1-4}$alkyl halide), for example, a $C_{1-10}$alkyl iodide such as methyl iodide, ethyl iodide, or propyl iodide (e.g., a $C_{1-4}$alkyl iodide), and a bromide (e.g., methyl bromide, and propyl bromide) or a chloride (e.g., methyl chloride) each corresponding to such an alkyl iodide]. Incidentally, the alkali metal halide (particularly the iodide) also functions a stabilizer for the carbonylation catalyst (e.g., the rhodium catalyst). These co-catalysts or accelerates may be used singly or in combination. Among them, the alkali metal halide, the alkyl halide, and/or the hydrogen halide, and others are preferred. The preferred catalyst system may comprise the metal catalyst component, and the alkyl halide and/or the hydrogen halide. It is preferred to use the metal catalyst component comprising the carbonylation catalyst (the metal catalyst) and the alkali metal halide (particularly the alkali metal iodide), the alkyl halide (particularly the alkyl iodide) and/or the hydrogen halide in combination. Moreover, if necessary, other co-catalyst or accelerator (the co-catalyst mentioned above) may be used in combination with such a catalyst system.

The content of the co-catalyst or the accelerator may be, for example, about 0.1 to 40% by weight, preferably about 0.5 to 30% by weight, and more preferably about 1 to 25% by weight, relative to the whole liquid phase system. More specifically, in the production of a carboxylic acid by a carbonylation reaction of the above-mentioned alcohol, the content of the alkyl halide such as methyl iodide may be, for example, about 1 to 25% by weight, preferably about 5 to 20% by weight, and more preferably about 5 to 15% by weight, relative to the whole liquid phase system. Incidentally, the higher the concentration of the alkyl halide is, the more the reaction is accelerated. In the light of the recovery of the alkyl halide, the plant size of a step for circulating the recovered alkyl halide to the reactor, the amount of energy necessary for the recovery or circulating, and others, an economically advantageous concentration may be suitably selected. Moreover, the content of the alkali metal halide such as lithium iodide may be, for example, about 0.1 to 40% by weight, preferably about 0.5 to 35% by weight, and more preferably about 1 to 30% by weight, relative to the whole liquid phase system.

Incidentally, in the reaction system, a carboxylic acid ester (particularly, an ester of a carboxylic acid with an alcohol, such as methyl acetate) may be contained in a proportion of about 0.1 to 20% by weight and preferably about 0.5 to 15% by weight relative to the whole liquid phase system. Incidentally, since the alcohol as a raw material and the carboxylic acid as a product are in equilibrium, about 0.5 to 10% by weight of the carboxylic acid ester usually exists in the reaction fluid.

Carbon monoxide to be fed to the reaction system may be used as a pure gas, or diluted with an inactive gas (e.g., nitrogen, helium, and carbon dioxide). Moreover, a carbon monoxide-containing waste gas component obtained from the succeeding step (e.g., a distillation step (distillation column)) may be recycled to the reaction system. The carbon monoxide partial pressure in the reaction system may be, for example, about 0.9 to 3 MPa (e.g., about 0.9 to 2 MPa), preferably about 1.15 to 2.5 MPa, and more preferably about 1.15 to 2 MPa (e.g., about 1.18 to 2 MPa) as an absolute pressure. Incidentally, carbon monoxide may be supplied by sparging from a lower part of the reactor.

In the carbonylation reaction, a shift reaction occurs due to a reaction of carbon monoxide and water, and hydrogen is generated. However, to the reaction system, hydrogen may be fed. Such hydrogen to be fed to the reaction system may be also fed to the reaction system as a mixed gas together with carbon monoxide as a raw material. Moreover, hydrogen may be fed by, if necessary, suitably purifying a gas component (containing hydrogen, carbon monoxide, and others) discharged in the succeeding distillation step (distillation column), and recycling the purified matter to the reaction system. The hydrogen partial pressure in the reaction system may be, for example, about 0.01 to 0.1 MPa, preferably about 0.014 to 0.07 MPa, and more preferably about 0.02 to 0.04 MPa (e.g., about 0.025 to 0.034 MPa) as an absolute pressure.

The carbon monoxide partial pressure or the hydrogen partial pressure in the reaction system may be adjusted, for example, by suitably regulating the feed rates of carbon monoxide and hydrogen to the reaction system, or the recycling amounts of these components to the reaction system, the feed rate of the raw material substrate (e.g., methanol) to the reaction system, the reaction temperature or pressure, and others.

Incidentally, although the carbon monoxide partial pressure and/or the hydrogen partial pressure in the reaction system may be arbitrarily adjusted by regulating the feed rate of carbon monoxide and/or hydrogen to the reaction system, large quantities of unreacted carbon monoxide are contained in offgas and the discharge amount also increases. Moreover, in the case where the hydrogen partial pressure rises, amounts of by-products such as acetaldehyde or methane increase. On the other hand, in the case where the feed rate of the substrate (e.g., methanol) is reduced, a producing amount of an objective carboxylic acid such as acetic acid is also reduced. Thereby, carbon monoxide remains in the reaction system excessively, and the carbon monoxide partial pressure increases. When the reaction temperature rises, the vapor pressure of the organic component is elevated and the carbon monoxide partial pressure and the hydrogen partial pressure are decreased. Moreover, when the reaction temperature is elevated, the producing amount of the objective carboxylic acid is increased. However, the producing amount of the by-product (e.g., acetaldehyde) is also increased, and additionally, the stability of the rhodium catalyst is deteriorated. Further, in the case where the reaction pressure increases, the carbon monoxide partial pressure and the hydrogen partial pressure are also elevated. That is, since the inner pressure of the reactor is elevated, it is necessary to design a fleshy reactor which is resistant to a high pressure, and therefore, the cost of equipment is increased. Moreover, as mentioned above, due to rise of the hydrogen partial pressure, the amount of the by-product such as acetaldehyde is increased.

In the carbonylation reaction, the reaction temperature may be, for example, about 100 to 250° C., preferably about 150 to 220° C., and more preferably about 170 to 210° C. Moreover, the reaction pressure may be about 1 to 5 MPa, preferably about 1.5 to 4 MPa, and more preferably about 2 to 3.5 MPa as a gauge pressure.

The reaction may be carried out in the presence or absence of a solvent. The reaction solvent is not particularly limited to a specific one as long as the reactivity, or the efficiency of separation or purification is not deteriorated, and a variety of solvents may be used. As the reaction solvent, a carboxylic acid (e.g., acetic acid) which is a product is usually employed in many cases.

Incidentally, in a conventional carbonylation reaction in which enough concentration of water exists, hydrogen is fully generated by a shift reaction between carbon monoxide and water, a low active Rh(III) catalyst which is generated on progression of the reaction is rapidly converted into an active species (Rh(I) catalyst), deterioration in catalyst activity as well as conversion of the Rh(III) catalyst into an insoluble component (e.g., rhodium iodide) are inhibited, and precipitation of the insoluble component is restrained. On the other hand, in the present invention, although a carbonylation reaction of an alcohol is carried out in the presence of a limited amount of water, and deterioration of the catalyst activity or precipitation of the insoluble component can be restrained even in the presence of such a limited amount of water.

The water content in the reaction system is, for example, about 0.1 to 10% by weight, preferably about 0.1 to 7% by weight, and more preferably about 0.1 to 5% by weight. Incidentally, the lower the water content is, the lower the amount of hydrogen produced by the shift reaction between carbon monoxide and water is, and as a result, generation of by-products (e.g., acetaldehyde, formic acid, propionic acid, and a hydrocarbon) can be inhibited. However, such a water content tends to induce deterioration of the reaction rate or unstabilization of the metal catalyst. In order to improve such defects, if necessary, to the reaction system may be added a compound formable of an iodide salt in the reaction system, such as an alkali metal halide (the above-mentioned alkali metal halide), a quaternary ammonium salt of an alkali metal, or a quaternary phosphonium salt of an alkali metal. Among these components, it is preferred to use the alkali metal iodide, particularly lithium iodide, in the light of solubility.

In the carbonylation reaction, a carboxylic acid having a carbon number of "n+1" (e.g., acetic acid) corresponding to an alcohol having a carbon number of "n" (e.g., methanol) is produced, and in addition, an ester of the produced carboxylic acid with the alcohol (e.g., methyl acetate), water involved in the esterification reaction, and further an aldehyde having a carbon number of "n+1" corresponding to the alcohol (e.g., acetaldehyde), and a carboxylic acid having a carbon number of "n+2" (e.g., propionic acid) are produced.

(Separation and Purification Step of Carboxylic Acid)

The reaction mixture (liquid reaction mixture) produced in the reaction system is continuously withdrawn from the reaction system (e.g., withdrawn from the bottom thereof), and introduced into a distillation step [a separation (and/or purification) step of a carboxylic acid (a distillation column)] through a feed line equipped with a valve. The distillation step may comprise a single distillation column (e.g., only a catalyst-separation column), or a plurality of distillation columns (e.g., combination of a catalyst-separation column and a carboxylic acid-purification column). Then, in the catalyst-separation column, at least a higher-boiling catalyst component (for example, a metal-containing catalyst component (a metal catalyst component), e.g., a carbonylation catalyst (a metal catalyst) such as a rhodium catalyst, and an alkali metal halide) is separated, and a lower-boiling component containing a carboxylic acid is separated as vapor.

The separation of the metal catalyst component may be carried out by a conventional separation method or a separator, and usually may be carried out by utilizing a distillation column (e.g., a plate column, a packed column, and a flash distillation column), a flasher (or an evaporator), or the like. Moreover, the metal catalyst component may be separated by a distillation method in combination with an industrially generalized method for collecting mist or solid.

The above-mentioned reaction mixture is separated into a vapor component as a lower-boiling component containing a reaction product and a liquid component as a higher-boiling component by distillation.

Incidentally, in the above-mentioned catalyst-separation column, in addition to the metal catalyst component, a higher-boiling component containing a carboxylic acid having a carbon number of "n+2" may be separated from the reaction mixture. Further, a metal catalyst component and a carboxylic acid having a carbon number of "n+2" may be separated from the separated higher-boiling component, respectively, and the separated metal catalyst component may be recycled to the reaction system.

Moreover, the distillation step, as the above-mentioned embodiment of FIG. 3, may comprise a catalyst-separation step (catalyst-separation column) for separating a metal catalyst component, and a carboxylic acid-purification step or a higher-boiling component-recovery step (a carboxylic acid-purification column) for separating a higher-boiling impurity such as a carboxylic acid having a carbon number of "n+2".

The lower-boiling component separated by the catalyst-separation column or the carboxylic acid-purification column may be used as a finished carboxylic acid product as it is. However, since the lower-boiling component contains a co-catalyst such as methyl iodide, an ester (e.g., methyl acetate) of an alcohol as a raw material with a carboxylic acid as a product, water, slight amounts of by-products [e.g., an aldehyde such as acetaldehyde, a carboxylic acid having a carbon number of "n+2" such as propionic acid, formic acid, a material which deteriorates a result of a potassium permanganate test (one of product specification of acetic acid), such as crotonaldehyde, an iodine ion, an alkyl iodide such as hexyl iodide] in addition to a carboxylic acid (e.g., acetic acid) as a product, the lower-boiling component may be subjected to a further separation or purification step to give a purified carboxylic acid.

More specifically, the lower-boiling component separated by the catalyst-separation column or the carboxylic acid-purification column (higher-boiling component-recovery column) may be further subjected to a lower-boiling component-recovery step (a lower-boiling component-recovery column) to recover a lower-boiling component (e.g., water, an ester such as methyl acetate, a co-catalyst such as methyl iodide, and an aldehyde having a carbon number of "n+1" n such as acetaldehyde, hereinafter sometimes simply referred to as a lower-boiling impurity) having a boiling point lower than that of the carboxylic acid (e.g., acetic acid), and in addition, to recover a carboxylic acid (e.g., acetic acid) as a higher-boiling component. The fraction containing the recovered lower-boiling impurity may be recycled to the reaction system. Moreover, the fraction containing the lower-boiling impurity may be further subjected to an aldehyde-recovery step (e.g., a distillation column) to remove an aldehyde therefrom, and then the residual component may be recycled to the reaction system.

The higher-boiling component containing the carboxylic acid separated by the lower-boiling component-recovery column may be recovered as a carboxylic acid which is a final product. Moreover, the lower-boiling component containing the carboxylic acid from the catalyst-separation column may be fed to the lower-boiling component-recovery column to separate a lower-boiling impurity therefrom. Thus obtained higher-boiling component containing the carboxylic acid may be further subjected to a carboxylic acid-purification step or a higher-boiling component-recovery step (a carboxylic acid-purification column) to remove a higher-boiling component (a higher-boiling impurity) such as a carboxylic acid having a carbon number of not less than "n+2" (e.g., propionic acid), which has a boiling point higher than that of the product carboxylic acid, and therefore, a higher purified carboxylic acid having a carbon number of "n+1" may be obtained.

Moreover, in the above-mentioned lower-boiling component-recovery step, if necessary, a separating property of a carboxylic acid such as acetic acid from water may be enhanced by adding an azeotrope with water, such as a carboxylic acid ester (e.g., methyl acetate) or an alkyl iodide (e.g., methyl iodide).

Incidentally, either the carboxylic acid-purification step or the lower-boiling component-recovery step may be carried out, or both of these steps may be carried out. The order of the carboxylic acid-purification step and the lower-boiling component-recovery step is not particularly limited to a specific one, and either of these steps may be conducted in advance of the other step. These steps are usually carried out after the catalyst-separation step.

The carboxylic acid-purification step and the lower-boiling component-recovery step may be carried out by utilizing a conventional separation method or separator, for example, a distillation column (e.g., a plate column, a packed column, and a flash distillation column) or others. Moreover, in the separation step of the carboxylic acid (a distillation step comprising a catalyst-separation step, a carboxylic acid-purification step, and the lower-boiling component-recovery step, and others) a vapor component and a liquid component may separated from the reaction mixture with or without heating. For example, in the case of utilizing a flash distillation, a vapor component and a liquid component can be separated from the reaction mixture, respectively, by depressurization without heating in an adiabatic flash distillation, and a vapor component and a liquid component can be separated from the reaction mixture, respectively, by heating and depressurization in an isothermal flash distillation, or these flash conditions may be combined to separate the reaction mixture. Such a flash distillation may be, for example, performed on the reaction mixture at a temperature of about 80 to 200° C. and a pressure (absolute pressure) of about 50 to 1000 kPa (for example, about 100 to 1000 kPa), preferably about 100 to 500 kPa, and more preferably about 100 to 300 kPa.

(Controlling Step of Carbon Monoxide and/or Hydrogen Concentration)

In the present invention, the proportion of a monovalent rhodium complex which is active in the reaction can be increased by maintaining the concentration (proportion) of carbon monoxide and/or hydrogen contained in the liquid phase (the reaction fluid) of the reaction system within a specific range. In addition, the precipitation of rhodium can be inhibited without increasing the hydrogen partial pressure in the reactor needlessly, the productivity of the carboxylic acid (e.g., acetic acid) in the reactor can be elevated, and the generation of by-products can be reduced. The concentration of carbon monoxide and hydrogen in the reaction fluid may be maintained at a constant level by not only a method of supplying a gas containing carbon monoxide and/or hydrogen to the reaction fluid in the process of being fed from the reactor to the flasher (or the distillation column), but also controlling of the carbon monoxide and/or hydrogen partial pressure, the reaction pressure, the reaction temperature in the reactor, the feed rate of the raw material, the recycling amount to the reactor, or others (for example, controlling these conditions within the above-described range).

The amount (proportion) of carbon monoxide contained in the liquid phase of the reaction system is about at least 2 mmol (e.g., about 2 to 60 mmol), preferably about 3 to 50 mmol, and more preferably about 3 to 40 mmol, relative to 1 kilogram of the liquid phase by weight per 1 MPa of carbon monoxide partial pressure of the reaction system. Moreover, the amount (proportion) of hydrogen contained in the liquid phase of the reaction system is at least about 50 mmol (e.g., about 50 to 300 mmol), preferably about 50 to 200 mmol, and more preferably about 70 to 200 mmol, relative to 1 kilogram of the liquid phase by weight per 1 MPa of hydrogen partial pressure of the reaction system. Incidentally, among the concentrations (proportions) of carbon monoxide and hydrogen contained in the liquid phase of the reaction system, it is sufficient that at least one concentration (proportion) is in the above-mentioned range, or both of these concentrations (proportions) may be in the above-mentioned range.

According to the present invention, an objective carboxylic acid such as acetic acid can be produced at a high formation rate (e.g., at a formation rate of not less than 10 mol/L/h (mol/(L·h)) as a space time yield) in spite of a low water content in the reaction system. Moreover, according to the present invention, generation of by-products can be also inhibited greatly. For example, the formation rate of an aldehyde (such as acetaldehyde) can be reduced to not more than $1/1500$ (e.g., about 0 to $1/1500$), preferably not more than $1/2100$ (e.g., about 0 to $1/2100$), and more preferably not more than $1/2300$ (e.g., about 0 to $1/2300$) as high as that of the objective carboxylic acid (e.g., acetic acid).

INDUSTRIAL APPLICABILITY

The present invention is useful for a process for industrially producing a carboxylic acid such as acetic acid, in particular, a process for producing a carboxylic acid by a continuous method.

EXAMPLES

The following examples are intended to describe this invention in further detail and should by no means be interpreted as defining the scope of the invention.

Comparative Example 1

To a reactor, reaction raw materials (methanol and carbon monoxide), a catalyst fluid, and lower-boiling materials (methyl iodide, methyl acetate, and water) were continuously fed, and the reaction was carried out under the following conditions: a reaction pressure of 3.0 MPaG (gauge pressure), a carbon monoxide partial pressure of 1.1 MPaA (absolute pressure), a hydrogen partial pressure of 0.025 MPaA (absolute pressure), and a reaction temperature of 194° C. The reaction fluid was introduced into a flasher at a feed rate of 2.00 kg/h, and the produced acetic acid and other lower-boiling materials were vaporized, and a higher-boiling component containing the catalyst component was circulated to the reactor by pressurizing with a pump.

The formation rate of acetic acid was 22.5 mol/L/h (mol/(L·h)). Moreover, carbon monoxide and hydrogen discharged from the flasher were 3.4 mmol/h and 2.0 mmol/h, respectively, and the unit partial pressures of carbon monoxide and hydrogen in the reaction fluid per unit weight (kg) of the reaction fluid were 1.5 mmol/kg/MPa (mmol/(kg·MPa)) and 40 mmol/kg/MPa (mmol/(kg·MPa)), respectively. The formation rate of acetaldehyde was 11 mmol/L/h (mmol/(L·h)), and was one-2100$^{th}$ as high as that of acetic acid.

In the outlet of the reactor, an infrared spectrum of the reaction fluid was measured, and the proportion of the monovalent rhodium complex in the reaction fluid was determined as 8 mol %. That is, the decreasing speed of the concentration of the rhodium catalyst was 1.61 mol %/h, and was too fast to carry on the reaction.

Example 1

To a reactor, reaction raw materials (methanol and carbon monoxide), a catalyst fluid, and lower-boiling materials (methyl iodide, methyl acetate, and water) were continuously fed, and the reaction was carried out under the following conditions: a reaction pressure of 3.5 MPaG, a carbon monoxide partial pressure of 1.7 MPaA, a hydrogen partial pressure of 0.028 MPaA, and a reaction temperature of 189° C. The reaction fluid was introduced into a flasher at a feed rate of 1.97 kg/h, and the produced acetic acid and other lower-boiling materials were vaporized, and a higher-boiling component containing the catalyst component was circulated to the reactor by pressurizing with a pump.

The formation rate of acetic acid was 23.1 mol/L/h (mol/(L·h)). Moreover, carbon monoxide and hydrogen discharged from the flasher were 11.4 mmol/h and 6.1 mmol/h, respectively, and the unit partial pressures of carbon monoxide and hydrogen in the reaction fluid per unit weight (kg) of the reaction fluid were 3.5 mmol/kg/MPa (mmol/(kg·MPa)) and 111 mmol/kg/MPa (mmol/(kg·MPa)), respectively. The formation rate of acetaldehyde was 9.3 mmol/L/h (mmol/(L·h)), and was one-2500th as high as that of acetic acid. The decreasing speed of the concentration of the rhodium catalyst was reduced to 0.47 mol %/h.

In the outlet of the reactor, an infrared spectrum of the reaction fluid was measured, and the proportion of the monovalent rhodium complex in the reaction fluid was determined as 40 mol %.

Example 2

To a reactor, reaction raw materials (methanol and carbon monoxide), a catalyst fluid, and lower-boiling materials (methyl iodide, methyl acetate, and water) were continuously fed, and the reaction was carried out under the following conditions: a reaction pressure of 3.5 MPaG, a carbon monoxide partial pressure of 1.9 MPaA, a hydrogen partial pressure of 0.031 MPaA, and a reaction temperature of 186° C. The reaction fluid was introduced into a flasher at a feed rate of 2.00 kg/h, and the produced acetic acid and other lower-boiling materials were vaporized, and a higher-boiling component containing the catalyst component was circulated to the reactor by pressurizing with a pump.

The formation rate of acetic acid was 23.6 mol/L/h (mmol/(L·h)). Moreover, carbon monoxide and hydrogen discharged from the flasher were 28.8 mmol/h and 8.4 mmol/h respectively, and the unit partial pressures of carbon monoxide and hydrogen in the reaction fluid per unit weight (kg) of the reaction fluid were 7.7 mmol/kg/MPa (mmol/(kg·MPa)) and 135 mmol/kg/MPa (mmol/(kg·MPa)), respectively. The formation rate of acetaldehyde was 5.4 mmol/L/h (mmol/(L·h)), and was one-4400th as high as that of acetic acid.

The proportion of the monovalent rhodium complex in the outlet of the reactor was calculated as the same manner as in Comparative Example 1, and determined as 43 mol %. The decreasing speed of the concentration of the monovalent rhodium catalyst was reduced to 0.12 mol %/h.

Example 3

To a reactor, reaction raw materials (methanol and carbon monoxide), a catalyst fluid, and lower-boiling materials (methyl iodide, methyl acetate, and water) were continuously fed, and the reaction was carried out under the following conditions: a reaction pressure of 3.0 MPaG (gauge pressure), a carbon monoxide partial pressure of 1.3 MPa (absolute pressure), a hydrogen partial pressure 0.029 MPa (absolute pressure), and a reaction temperature of 187° C. The reaction fluid was introduced into a flasher at a feed rate of 2.00 kg/h, and the produced acetic acid and other lower-boiling materials were vaporized, and a higher-boiling component containing the catalyst component was circulated to the reactor by pressurizing with a pump.

The formation rate of acetic acid was 19.7 mol/L/h (mol/(L·h)). Moreover, carbon monoxide and hydrogen discharged from the flasher were 31.7 mmol/h and 7.4 mmol/h, respectively, and the unit partial pressures of carbon monoxide and hydrogen in the reaction fluid per unit weight (kg) of the reaction fluid were 12 mmol/kg/MPa (mmol/(kg·MPa)) and 128 mmol/kg/MPa (mmol/(kg·MPa)), respectively. The formation rate of acetaldehyde was 5.5 mmol/L/h (mmol/(L·h)), and was one-3600th as high as that of acetic acid.

The proportion of the monovalent rhodium complex in the outlet of the reactor was calculated as the same manner as in Comparative Example 1, and determined as 48 mol %. The decreasing speed of the concentration of the monovalent rhodium catalyst was 0.08 mol %/h.

Example 4

To a reactor, reaction raw materials (methanol and carbon monoxide), a catalyst fluid, and lower-boiling materials (methyl iodide, methyl acetate, and water) were continuously fed, and the reaction was carried out under the following conditions: a reaction pressure of 3.0 MPaG, a carbon monoxide partial pressure of 1.3 MPaA, a hydrogen partial pressure of 0.030 MPaA, and a reaction temperature of 189° C. The reaction fluid was introduced into a flasher at a feed rate of 2.06 kg/h, and the produced acetic acid and other lower-boiling materials were vaporized, and a higher-boiling component containing the catalyst component was circulated to the reactor by pressurizing with a pump.

The formation rate of acetic acid was 20.0 mol/L/h (mol/(L·h)). Moreover, carbon monoxide and hydrogen discharged from the flasher were 33.9 mmol/h and 6.5 mmol/h, respectively, and the unit partial pressures of carbon monoxide and hydrogen in the reaction fluid per unit weight (kg) of the reaction fluid were 13 mmol/kg/MPa (mmol/(kg·MPa)) and 105 mmol/kg/MPa (mmol/(kg·MPa)), respectively. The formation rate of acetaldehyde was 5.1 mmol/L/h (mmol/(L·h)), and was one-3900th as high as that of acetic acid.

The proportion of the monovalent rhodium complex in the outlet of the reactor was calculated as the same manner as in Comparative Example 1, and determined as 52 mol %. The decreasing speed of the concentration of the monovalent rhodium catalyst was 0.07 mol %/h.

Example 5

To a reactor, reaction raw materials (methanol and carbon monoxide), a catalyst fluid, and lower-boiling materials (methyl iodide, methyl acetate, and water) were continuously fed, and the reaction was carried out under the following conditions: a reaction pressure of 2.7 MPaG, a carbon monoxide partial pressure of 1.2 MPaA, a hydrogen partial pressure of 0.030 MPaA, and a reaction temperature of 187° C. The reaction fluid was introduced into a flasher at a feed rate of 2.00 kg/h, and the produced acetic acid and other lower-boiling materials were vaporized, and a higher-boiling component containing the catalyst component was circulated to the reactor by pressurizing with a pump.

The formation rate of acetic acid was 12.0 mol/L/h (mol/(L·h)). Moreover, carbon monoxide and hydrogen discharged from the flasher were 57.9 mmol/h and 4.7 mmol/h, respectively, and the unit partial pressures of carbon monoxide and hydrogen in the reaction fluid per unit weight (kg) of the reaction fluid were 24 mmol/kg/MPa (mmol/(kg·MPa)) and 81 mmol/kg/MPa (mmol/(kg·MPa)), respectively. The formation rate of acetaldehyde was 3.2 mmol/L/h (mmol/(L·h)), and was one-3700th as high as that of acetic acid.

The proportion of the monovalent rhodium complex in the outlet of the reactor was calculated as the same manner as in Comparative Example 1, and determined as 45 mol %. The decreasing speed of the concentration of the monovalent rhodium catalyst was 0.11 mol %/h.

Example 6

To a reactor, reaction raw materials (methanol and carbon monoxide), a catalyst fluid, and lower-boiling materials (methyl iodide, methyl acetate, and water) were continuously fed, and the reaction was carried out under the following conditions: a reaction pressure of 3.0 MPaG, a carbon monoxide partial pressure of 1.5 MPaA, a hydrogen partial pressure of 0.034 MPaA, and a reaction temperature of 195° C. The reaction fluid was introduced into a flasher at a feed rate of 2.01 kg/h, and the produced acetic acid and other lower-boiling materials were vaporized, and a higher-boiling component containing the catalyst component was circulated to the reactor by pressurizing with a pump.

The formation rate of acetic acid was 22.7 mol/L/h (mol/(L·h)). Moreover, carbon monoxide and hydrogen discharged from the flasher were 8.7 mmol/h and 5.8 mmol/h, respectively, and the unit partial pressures of carbon monoxide and hydrogen in the reaction fluid per unit weight (kg) of the reaction fluid were 2.9 mmol/kg/MPa (mmol/(kg·MPa)) and 85 mmol/kg/MPa (mmol/(kg·MPa)), respectively. The formation rate of acetaldehyde was 10.1 mmol/L/h (mmol/(L·h)), and was one-2200th as high as that of acetic acid.

The proportion of the monovalent rhodium complex in the outlet of the reactor was calculated as the same manner as in Comparative Example 1, and determined as 62 mol %. The decreasing speed of the concentration of the monovalent rhodium catalyst was 0.04 mol %/h.

Example 7

To a reactor, reaction raw materials (methanol and carbon monoxide), a catalyst fluid, and lower-boiling materials (methyl iodide, methyl acetate, and water) were continuously fed, and the reaction was carried out under the following conditions: a reaction pressure of 3.0 MPaG, a carbon monoxide partial pressure of 1.4 MPaA, a hydrogen partial pressure of 0.020 MPaA, and a reaction temperature of 195° C. The reaction fluid was introduced into a flasher at a feed rate of 2.02 kg/h, and the produced acetic acid and other lower-boiling materials were vaporized, and a higher-boiling component containing the catalyst component was circulated to the reactor by pressurizing with a pump.

The formation rate of acetic acid was 19.2 mol/L/h (mol/(L·h)). Moreover, carbon monoxide and hydrogen discharged from the flasher were 8.5 mmol/h and 4.3 mmol/h, respectively, and the unit partial pressures of carbon monoxide and hydrogen in the reaction fluid per unit weight (kg) of the reaction fluid were 3.0 mmol/kg/MPa (mmol/(kg·MPa)) and 74 mmol/kg/MPa (mmol/(kg·MPa)), respectively. The formation rate of acetaldehyde was 6.7 mmol/L/h (mmol/(L·h)), and was one-2900th as high as that of acetic acid.

The proportion of the monovalent rhodium complex in the outlet of the reactor was calculated as the same manner as in Comparative Example 1, and determined as 60 mol %. The decreasing speed of the concentration of the monovalent rhodium catalyst was 0.10 mol %/h.

The formations of the catalyst fluids used in Examples and Comparative Examples are shown in Table 1. Incidentally, as the rhodium catalyst, a Rh·I·carbonyl complex was used. Moreover, the results obtained in Examples and Comparative Examples are shown in Table 2.

TABLE 1

|  | Rh (wt ppm) | LiI (wt %) | MeI (wt %) | $H_2O$ (wt %) | MA (wt %) | AC (wt %) |
| --- | --- | --- | --- | --- | --- | --- |
| Com. Ex. 1 | 620 | 11.6 | 12.2 | 2.8 | 8.0 | 65 |
| Ex. 1 | 610 | 11.5 | 14.5 | 2.6 | 7.5 | 64 |
| Ex. 2 | 750 | 10.9 | 14.0 | 1.7 | 5.2 | 68 |
| Ex. 3 | 870 | 9.5 | 10.6 | 2.5 | 6.6 | 71 |
| Ex. 4 | 850 | 9.7 | 13.0 | 1.9 | 5.8 | 70 |
| Ex. 5 | 660 | 10.3 | 14.4 | 2.6 | 7.3 | 65 |
| Ex. 6 | 860 | 14.2 | 9.2 | 1.3 | 4.0 | 71 |
| Ex. 7 | 760 | 13.9 | 9.8 | 1.6 | 4.8 | 70 |

In Table 1, "MeI", "MA", and "AC" represent methyl iodide, methyl acetate, and acetic acid, respectively.

TABLE 2

|  | Reactor | | | | Formation rate | | | Discharged amount from flasher | | Concentration in reaction fluid | | Rh(I)/ Rh(III) Molar ratio | Precipitation of Rh mol %/h |
| --- | --- | --- | --- | --- | --- | --- | --- | --- | --- | --- | --- | --- | --- |
|  | Total pressure MPaG | Partial pressure of CO MPaA | Partial pressure of $H_2$ MPaA | Temperature ° C. | Amount withdrawn from bottom kg/h | Acetic acid mol/(L·h) | AD | AC/AD | CO mmol/h | $H_2$ mmol/h | CO mmol/(kg·MPa) | $H_2$ | | |
| Com. Ex. 1 | 3.0 | 1.1 | 0.025 | 194 | 2.00 | 22.5 | 0.011 | 2045 | 3.4 | 2.0 | 1.5 | 40 | 0.08 | 1.61 |
| Ex. 1 | 3.5 | 1.7 | 0.028 | 189 | 1.97 | 23.1 | 0.0093 | 2484 | 11.4 | 6.1 | 3.5 | 111 | 0.40 | 0.47 |

TABLE 2-continued

| | | Reactor | | | | Formation rate | | | Discharged amount from flasher | | Concentration in reaction fluid | | Rh(I)/ | Precipitation |
| | Total pressure MPaG | Partial pressure of CO MPaA | Partial pressure of H$_2$ MPaA | Temperature °C. | Amount withdrawn from bottom kg/h | Acetic acid mol/(L·h) | AD mol/(L·h) | AC/AD | CO mmol/h | H$_2$ mmol/h | CO mmol/(kg·MPa) | H$_2$ mmol/(kg·MPa) | Rh(III) Molar ratio | of Rh mol %/h |
|---|---|---|---|---|---|---|---|---|---|---|---|---|---|---|
| Ex. 2 | 3.5 | 1.9 | 0.031 | 186 | 2.00 | 23.6 | 0.0054 | 4370 | 28.8 | 8.4 | 7.7 | 135 | 0.43 | 0.12 |
| Ex. 3 | 3.0 | 1.3 | 0.029 | 187 | 2.00 | 19.7 | 0.0055 | 3582 | 31.7 | 7.4 | 12 | 128 | 0.48 | 0.08 |
| Ex. 4 | 3.0 | 1.3 | 0.030 | 189 | 2.06 | 20.0 | 0.0051 | 3922 | 33.9 | 6.5 | 13 | 105 | 0.52 | 0.07 |
| Ex. 5 | 2.7 | 1.2 | 0.03 | 187 | 2.00 | 12.0 | 0.0032 | 3750 | 57.9 | 4.7 | 24 | 81 | 0.45 | 0.11 |
| Ex. 6 | 3.0 | 1.5 | 0.034 | 195 | 2.01 | 22.7 | 0.0101 | 2200 | 8.7 | 5.8 | 2.9 | 85 | 0.62 | 0.04 |
| Ex. 7 | 3.0 | 1.4 | 0.020 | 195 | 2.02 | 19.2 | 0.0067 | 2900 | 8.5 | 4.3 | 3.0 | 74 | 0.60 | 0.10 |

In Table 2, "AC" represents acetic acid, and "AD" represents acetaldehyde.

The invention claimed is:

1. A process for producing a carboxylic acid having a carbon number of "n+1" which comprises
    allowing an alcohol having a carbon number of "n" or a derivative thereof to continuously react with carbon monoxide in the presence of a catalyst system comprising a metal catalyst component, and an alkyl halide and/or hydrogen halide, and a limited amount of water, in a reaction system,
    continuously withdrawing the reaction mixture from the reaction system,
    introducing the withdrawn reaction mixture into a distillation step, and
    separating a higher-boiling component at least containing the metal catalyst component and a lower-boiling component containing a carboxylic acid having a carbon number of "n+1", respectively,
    wherein the amount of carbon monoxide contained in a liquid phase of the reaction system relative to 1 kilogram of the liquid phase by weight is at least 2 mmol per 1 MPa of carbon monoxide partial pressure of the reaction system, and
    the carbon monoxide partial pressure of the reaction system is 0.9 to 3 MPa.

2. A process according to claim 1, wherein the reaction of the alcohol or the derivative thereof with carbon monoxide is carried out in the presence of water of 0.1 to 10% by weight relative to the whole liquid phase of the reaction system.

3. A process according to claim 1, wherein the amount of hydrogen contained in a liquid phase of the reaction system relative to 1 kilogram of the liquid phase by weight is at least 50 mmol per 1 MPa of hydrogen partial pressure of the reaction system, and the hydrogen partial pressure is 0.01 to 0.1 MPa.

4. A process according to claim 1, wherein the reaction is carried out in the presence of the catalyst system comprising a catalyst composed of a metal of the group 8 of the Periodic Table of Elements, an alkali metal iodide, and an alkyl iodide to produce acetic acid at a formation rate of at least 10 mol/L/h, and a liquid reaction mixture is continuously withdrawn, and introduced into the distillation step having a pressure lower than the pressure of the reaction system.

5. A process according to claim 1, wherein the carboxylic acid having a carbon number of "n+1" is acetic acid, and the formation rate of acetaldehyde as a by-product is one-2100th or less as high as that of acetic acid.

6. A process according to claim 1, which comprises allowing methanol to continuously react with carbon monoxide in the presence of the catalyst system comprising a catalyst composed of a metal of the group 8 of the Periodic Table of Elements, lithium iodide and methyl iodide, and 0.1 to 5% by weight of water relative to the whole liquid phase in the reaction system to produce acetic acid, wherein the amount of carbon monoxide contained in the liquid phase of the reaction system relative to 1 kilogram of the liquid phase by weight is 2 to 50 mmol per 1 MPa of carbon monoxide partial pressure of the reaction system, the amount of hydrogen contained in the liquid phase of the reaction system relative to 1 kilogram of the liquid phase by weight is 50 to 400 mmol per 1 MPa of hydrogen partial pressure of the reaction system, the formation rate of acetic acid is at least 18 mol/L/h, and the formation rate of acetaldehyde as a by-product is one-2300th or less as high as that of acetic acid.

7. A process according to claim 1, wherein the distillation step comprises a catalyst-separation step, and a carboxylic acid-purification step; the reaction mixture withdrawn from the reaction system is introduced into the catalyst-separation step to separate the higher-boiling component containing the metal catalyst component and the lower-boiling component containing a carboxylic acid having a carbon number of "n+1", respectively; and the lower-boiling component is introduced into the carboxylic acid-purification step to separate a higher-boiling impurity, a lower-boiling component containing a carboxylic acid having a carbon number of "n+1", and a waste gas component at least containing carbon monoxide and hydrogen, respectively.

8. A method for inhibiting precipitation of a metal catalyst and generation of a by-product with improving a formation rate of a carboxylic acid having a carbon number of "n+1" in a process for producing the carboxylic acid, said process comprises
    allowing an alcohol having a carbon number of "n" or a derivative thereof to continuously react with carbon monoxide in the presence of a catalyst system comprising a metal catalyst component, and an alkyl halide and/or hydrogen halide, and a limited amount of water, in the reaction system,
    continuously withdrawing the reaction mixture from the reaction system,
    introducing the withdrawn reaction mixture into a distillation step, and
    separating a higher-boiling component at least containing the metal catalyst component and a halide salt from a lower-boiling component containing a carboxylic acid having a carbon number of "n+1", respectively.

wherein the method comprises adjusting an amount of carbon monoxide contained in a liquid phase of the reaction system relative to 1 kilogram of the liquid phase by weight is at least 2 mmol per 1 MPa of carbon monoxide partial pressure of the reaction system under the carbon monoxide partial pressure of 0.9 to 3 MPa of the reaction system.

9. The process according to claim 1, wherein the metal catalyst component comprises a rhodium catalyst.

* * * * *